(12) United States Patent
Yazawa et al.

(10) Patent No.: US 7,163,822 B2
(45) Date of Patent: Jan. 16, 2007

(54) APPARATUS AND METHOD FOR LUMINOMETRIC ASSAY

(75) Inventors: Yoshiaki Yazawa, Nishitokyo (JP); Hideki Kambara, Hachioji (JP); Masao Kamahori, Kokubunji (JP); Kunio Harada, Hachioji (JP); Kazunori Okano, Shiki (JP)

(73) Assignee: Hitachi, Ltd., Tokyo (JP)

( * ) Notice: Subject to any disclaimer, the term of this patent is extended or adjusted under 35 U.S.C. 154(b) by 646 days.

(21) Appl. No.: 10/338,899

(22) Filed: Jan. 9, 2003

(65) Prior Publication Data
US 2003/0219891 A1 Nov. 27, 2003

(30) Foreign Application Priority Data
May 14, 2002 (JP) ............................. 2002-138729

(51) Int. Cl.
C12M 1/34 (2006.01)
(52) U.S. Cl. ............................. 435/287.2; 435/288.7; 435/808; 422/52; 257/292; 348/241
(58) Field of Classification Search ............ 435/288.7; 348/241, 243, 308
See application file for complete search history.

(56) References Cited
U.S. PATENT DOCUMENTS
4,700,231 A * 10/1987 Matsumoto ................. 348/245

| 6,365,950 | B1 * | 4/2002 | Sohn ........................... 257/431 |
| 6,597,525 | B1 * | 7/2003 | Kubota ........................ 359/885 |
| 6,770,441 | B1 * | 8/2004 | Dickinson et al. ............. 435/6 |
| 2003/0052982 | A1 * | 3/2003 | Chieh ......................... 348/302 |

FOREIGN PATENT DOCUMENTS

| JP | 9-72843 | 9/1995 |
| WO | WO 9927140 A1 * | 6/1999 |
| WO | WO 00/37684 A1 | 12/1999 |
| WO | WO 00/79008 A2 | 6/2000 |

OTHER PUBLICATIONS

Victor Lyamichev, Mary Ann D. Brow and James E. Dahlberg, "Structure-Specific Endonucleolytic Cleavage of Nucleic Acids by Eubacterial DNA Polymerases", Science, vol. 260 (May 7, 1993) pp. 778-783.

(Continued)

*Primary Examiner*—William H. Beisner
(74) *Attorney, Agent, or Firm*—Reed Smith LLP; Stanley P. Fisher, Esq.; Juan Carlos A. Marquez, Esq.

(57) ABSTRACT

A small sized, cost-effective genetic testing apparatus that provides high sensitivity testing, for performing genetic testing simply and at low cost. An optical sensor array for the apparatus and method for luminometric assay comprises a means that simultaneously selects 2 pixels and detects minute amounts of chemiluminescence by obtaining the differential output of the respective signals.

14 Claims, 26 Drawing Sheets

OTHER PUBLICATIONS

Timothy Morris, Betty Robertson, and Margaret Gallagher, "Rapid Reverse Transcription-PCR Detection of Hepatitis C Virus RNA in Serum by Using the TaqMan Fluorogenic Detection System", Journal of Clinical Microbiology, Dec. 1996,1 pp. 2933-2936.

Patrick O. Brown and Leland Hartwell, "Genomics and Human Disease—Variations on Variation", Nature Genetics, vol. 18 (Feb. 18, 1998), pp. 91-93.

Mostafa Ronaghi, Mathias Uhlén and Pal Nyrén, "A Sequencing Method Based on Real-Time Pyrophosphate", Science, vol. 281 (Jul. 17, 1998), pp. 363 and 365.

Sunetra Mendis, Sabrine E. Kemeny and Eric R. Fossum, "CMOS Active Pixel Image Sensor", IEEE Transactions on Electron Devices, vol. 41, No. 3, Mar. 1994, pp. 452-453.

Guo-hua Zhou,, Masao Kamahori, Kazunori Okano, Gao Chuan, Kunio Harada and Hideki Kambara, "Quantitative Detection of Single Nucleotide Polymorphisms for a Pooled Sample by a Bioluminometric Assay Coupled with Modified Primer Extension Reactions (BAMPER)", Nucleic Acids Research, 2001, vol. 29, No. 19, pp. 1-11.

* cited by examiner

○ TARGET SAMPLE
◉ CONTROL SAMPLE

EXTENSION REACTION

CHMEMILUMINESCENCE REACTION

⇩ WASH

⇩ ADD REAGENT

⇩ EXTENSION REACTION OF N

CHMEMILUMINESCENCE

APPARATUS AND METHOD FOR LUMINOMETRIC ASSAY

BACKGROUND OF THE INVENTION

1. Field of the Invention

The present invention relates to an apparatus and system for DNA detection such as detection of single nucleotide mutations, gene diagnosis, genetic typing or detecting biological substances such as protein and ATP.

2. Description of the Related Art

Analysis of the human genome sequence is almost completed, and activity is increasing in efforts to put genetic information to practical use in the medical field in areas such as diagnosis. Following the analysis of the genome sequence, gene expression profile analysis and analysis of single nucleotide polymorphisms (SNPs) in genes are now attracting attention. By examining genes expressing under a variety of conditions and investigating gene mutations of a variety of solid bodies, genetic functions and the relation between genes and disease or genes and sensitivity to pharmaceuticals can be investigated. Further, the diagnosis of disease and the like is now being carried out using such accumulated knowledge about genes.

Unlike analysis of unknown genes, in diagnosis of disease the object of investigation is a known gene or the presence or absence of a mutation thereof. It is desirable that such investigation can be performed at a low cost, and various methods have been developed to achieve this. In medical diagnosis, examination of disease occurring due to the influence of a variety of genes and environments as well as examination of genes related to sensitivity to pharmaceuticals is becoming more important than diagnosis of disease caused by a single gene. To achieve this, it is important to simultaneously analysis a variety of types of genes. Accordingly, it is necessary to examine a plurality of genes, and not just a single gene or mutation, and a method is thus required that determines SNPs and the like at a low cost that includes the amplification process of an assay site of the gene. Methods reported as practicable in analysis of SNPs and probe assay of genes include Invader assay (Science 260, 778 (1993)), TaqMan assay (J. Clin. Microbiol. 34, 2933 (1996)), DNA microarrays (Nature Gent. 18, 91 (1998)), pyrosequencing (Science 281, 363 (1998)) and the like. The first 3 methods mentioned are detection methods that use fluorescence labeling, and employ an excitation laser light source and a light sensor system. In contrast, pyrosequencing is a method that uses stepwise complementary strand synthesis and chemiluminescence, and employs a system that sequentially injects trace amounts of nucleic acid substrate and a light sensor system, and does not require an excitation light source.

FIG. 1 shows an example of a configuration of an apparatus for measuring chemiluminescence used in a conventional method. As a detector 260 used as a mechanism for detecting luminescence from a plurality of reaction baths 101 on a sample plate 100, for example, a photomultiplier tube is used. From a container 133 containing sample DNA, a sample is dispensed to each of the reaction baths 101 on sample plate 100 by means of a pipette 135. Next, a reagent solution containing primers corresponding to a plurality of measurement items is dispensed from a container 131 by means of a pipette 134. To prevent contamination with a different reagent, pipette 134 is washed in lavage fluid of a container 132. To detect luminescence induced in the reaction baths in accordance with matching between a reagent and sample, detector 260 scans the reaction baths by means of a moving device 136. Because a device to move the detector or the sample plate is indispensable in this apparatus, it is difficult to implement miniaturization, cost reduction and increased throughput.

As a light-sensitive detector to measure faint light, in general, a photomultiplier tube, charge-coupled device (CCD) or MOS-type sensor or the like is mainly used. While a significant advantage can be obtained by the use of a photomultiplier tube, it requires a high voltage, and integration is also a problem, and thus it is not suitable for a small-sized apparatus. In contrast, large-scale integration is possible with a semiconductor sensor, and it also operates on a low voltage and low current and is therefore suitable for miniaturization of an apparatus. Apart from the case of an avalanche photodiode, which is not suitable for integration as the production process thereof is complicated, for a semiconductor sensor, the quantum efficiency of a commonly used CCD or photodiode is at highest 1, which is low compared to the photomultiplier tube. To enhance the S/N ratio a strategy that effectively utilizes chemiluminescence is required.

In measuring luminescence from a biological sample, it is necessary to amplify only the signal of interest under a measurement condition of a high background light intensity. Further, in the case of measurement by a charge storage technique using a photodiode as a detector, because the potential decrement from a charging potential of about 1–5 V becomes the signal output, to perform a large amplification for a micro-signal, a mechanism to cancel the charging potential is necessary to prevent saturation of the amplifier. Due to such necessity, a technique is used which measures a reference signal along with the signal from the sample of interest, and enhances the S/N ratio by conducting differential amplification of these signals. At this time, a method can be employed in which a specific location on the sample plate is defined as a control pixel, and which then determines the differential amplification of the signal from the sample of interest using the control pixel as a basis. Alternatively, a method can be employed in which a signal is read in a condition where light is not irradiated to the sensor, this signal is then stored in a temporary capacitor for record, and then a signal light is irradiated and the differential amplification between that signal and the previously stored signal is determined (IEEE Transactions on electron devices vol. 41, 452 (1994)). In the former method, there is no flexibility in the selection of a control pixel and there is also difficulty in terms of usability in measuring relative luminescence intensity from a plurality of different samples. In the latter method, there is difficulty involved in the constitution of a capacitor that can retain an electric charge even for a signal accumulated over several seconds, and also in obtaining high measurement accuracy that excludes the influence of dark current fluctuations. Therefore, there is a need for an advanced correction method that solves these problems.

The realization of measurement with high throughput is essential to prepare for greater utilization of DNA diagnosis, such as that concerning SNPs. However, while simultaneous measurement of a plurality of items is effective, in measurement that utilizes chemiluminescence, conventionally, for each reaction bath on a sample plate, reaction of one type of sample and probe has been performed, and it has been difficult to obtain high throughput for a large number of assay items or a large number of samples.

SUMMARY OF THE INVENTION

For a DNA testing system for medical diagnosis, it is required that (1) a small amount sample is required and the cost of reagents is low, (2) simultaneous testing of a plurality of DNA sites is possible, (3) mutation of 1 nucleotide can be distinguished and detected, and (4) a signal detection apparatus be small-size and low-cost.

In a detection system using DNA microarrays that can test a large number of sites, fluorescence analysis is commonly used. Thus, the signal detection part thereof comprises an excitation light source such as a laser or halogen lamp, a fluorescence detection part, an optical system and a moving mechanism of a sample stage. However, the optical system relating to the excitation light source is a significant obstacle to miniaturization of the detection part. A detection method using chemiluminescence, such as the previously proposed pyrosequence technique or BAMPER (bioluminometric assay with modified primer extension reactions) technique (Nucleic Acid Research vol. 29, e93 (2001)) or the like, does not require a light source for excitation, and thus enables miniaturization of a detection part. For example, the flow of detection of SNPs using BAMPER is shown in FIG. 2. A wildtype probe DNA 302 and a mutant probe DNA 304 are hybridized to a target 301, and depending on whether the target is a wildtype or a mutant, complementary strand syntheses is allowed to proceed 303 or not proceed (or the reverse thereof). Inorganic pyrophosphate 307 generated along with synthesis of the complementary strand is converted to ATP, and by the reaction thereof with luciferin, chemiluminescence is obtained and determined. Although this is an extremely simple and easy method, as in the conventional method, high sensitivity is required for the detector. As a signal detection means, a photomultiplier tube or cooled CCD (charge coupled device) are already widely used, however it has been difficult to carry out miniaturization and cost reduction while maintaining high sensitivity. Moreover, in the conventional signal detection method, to accurately determine a slight difference in signal intensity between two samples it has been necessary to use a procedure that separately measures each of the signals and then compares the measurement values. To solve these problems, there is a need for a novel method and assay system that can perform high sensitivity measurement of the signals of two samples simply and quickly. Further, to realize assaying with high throughput by simultaneous measurement of a plurality of items, there is a need for a structure that enables simple processing of a large number of assay items or samples at the same time.

As a means for solving these problems, the present invention characteristically embodies (1) a structure in which a light-sensitive detector comprises a photodiode array to efficiently capture luminescence from a plurality of samples, wherein each of the biological samples is brought into a one-to-one correspondence with a pixel of the light-sensitive detector, and the detector is disposed appressed against a sample plate, (2), a mechanism comprising 2 or more decoders as pixel addressing means for addressing an arbitrary pixel to conduct differential amplification of output in order to accurately determine faint luminescence emitted from a sample, wherein the mechanism simultaneously detects a signal from a sample of interest and a signal from a control sample and conducts differential amplification of the detected signals, (3) a mechanism that carries out reaction with differing probes by a single dispensing of a sample, by providing as subcells a plurality of small sections in each reaction bath on a sample plate to which a sample is added, to realize fast determination of a small amount of sample.

In a conventional apparatus to detect luminescence from a plurality of samples at high sensitivity, a photomultiplier tube is used as a detector and a signal is read by moving a sample plate or a photoreceptive optical system such that the reaction baths on the sample plate and a photoreceptive part are optically coupled in sequence. In measurement performed with DNA as an object, fluorescence is mostly used, typically using microarrays, and excitation light is required. Since excitation light is background noise in detecting the signal light, it is necessary to eliminate excitation light by providing a filter or spectroscope in front of the optical sensor, and a certain space must thus be maintained between the detector and sample.

In contrast to the above, because an assay method using chemiluminescence does not require excitation light, the optical system can be significantly simplified and, moreover, the optical sensor and sample can be brought into close proximity with each other. Examples of assay methods using chemiluminescence include the BAMPER technique. In BAMPER, probe DNA is hybridized to a target and depending on whether the target is a wildtype or mutant, complementary strand synthesis is allowed to proceed or not proceed (or the reverse thereof). Inorganic pyrophosphate generated in the case where complementary strand synthesis has occurred is converted to ATP, and this is reacted with luciferin to obtain chemiluminescence, which is then measured. In the present invention, an optical sensor array comprising a plurality of optical sensors is used, and the sample plate and optical sensor array substrate are fixed together such that the reaction baths and pixels of the optical sensor array correspond one-to-one in the vertical direction. According to the present invention, there is provided a structure that reads light generated in a reaction bath appressed thereto by means of the optical sensor of the pixel that has been selected. Thus, a moving mechanism of a sample plate or optical system becomes unnecessary, and the apparatus is significantly simplified. Further, optical coupling between a sample and optical sensor is strengthened, thus enabling enhancement of detection sensitivity.

Using an optical sensor array comprising a plurality of optical sensors, by amplifying the difference in luminescence from a sample of interest and from a control sample it is possible to significantly enhance the effectual measurement sensitivity. In genetic testing by means of chemiluminescence, highly precise detection of minute variations among samples is required. Therefore, a feature is herein disclosed that simultaneously selects a sample pixel at an arbitrary location on a sample plate and a control pixel, and performs differential amplification of the signals of the two pixels. Using an optical sensor array provided with 2 independent decoders, comprising a decoder (referred to as "S-decoder") that selects a pixel to detect a signal of a sample of interest and a decoder (referred to as "C-decoder") that selects a pixel to detect a signal of a control sample, a signal from the pixel corresponding to the sample of interest and a signal from the pixel corresponding to the control sample are output to respectively independent signal lines. Thus, an offset factor that is common among the selected cells can be cancelled to enable amplification of high amplitude, thereby enabling enhancement of the detection sensitivity of faint light. While BAMPER is an extremely simple and easy method, because each site is determined independently when assaying a large number of DNA sites, improvement to facilitate labor saving is required. Specifically, it is necessary to enable simple and easy testing of various probe regions at the same time. In order to solve this problem, the present invention provides a system in which a plurality of small sub-reaction baths are provided in a reaction bath to perform determination of each one of various DNA sites of interest. Although hybridization reaction is conducted in one operation, the present invention realizes a system in which complementary strand synthesis reaction and luminescence reaction caused by a plurality of reactions are performed simultaneously, but are nevertheless distinguished from each. A different probe or target is retained in each subcell, and following hybridization of the target or probe complementary strand synthesis reaction proceeds. The complementary strand synthesis reaction is carried out in each cell in an almost isolated state. To that end, the constitution and conditions employed are such that a reaction solution of complementary strand synthesis and the accompanying chemiluminescence does not leak to outside the cell. If inorganic pyrophosphate (PPi) produced as a byproduct of complementary strand synthesis reaction flows into a different cell, it is impossible to know where the complementary strand synthesis occurred, that is, whether or not a target was present. When hybridizing a target, the solution containing the target can flow freely among all of the cells. However, after hybridization, complementary strand synthesis is carried out with each subcell in an isolated state. This is achieved by adhering a separating plate to the top part of the subcells. Chemiluminescence from the respective subcells is distinguished and detected, to simultaneously perform assay of a plurality of DNA sites.

DESCRIPTION OF THE PREFERRED EMBODIMENTS

In this description, the constitution of a small-sized detection apparatus of high sensitivity that is effective in chemiluminescence detection that simultaneously assays a plurality of target regions or DNA is described first. Herein, a means is disclosed that enhances the sensitivity of a detection system and enables miniaturization of the apparatus by bringing reaction baths and pixels of a light-sensitive detector into a one-to-one correspondence and disposing them in close contact with each other. Thereafter, a means is described for determining the luminescence signal accompanying an extension reaction of a nucleotide at high detection sensitivity. The means comprises a pixel addressing means composed of 2 systems as an optical sensor array, wherein one of the systems addresses a control pixel and the other addresses a target-sample pixel, and by simultaneously outputting the signals from the 2 pixels and obtaining the differential output thereof, a signal based on nucleotide extension, specifically, gene mutation, is extracted.

Finally, a system is disclosed for assaying many target regions or DNA at the same time, wherein PCR amplification is conducted for each target, single strand DNA is formed, and then the DNA is dispensed into each reaction bath to carry out BAMPER determination. Conventionally, it has been necessary to carry out BAMPER or SNP determination the same number of times as the number of targets. However, a means is disclosed herein that performs amplification of targets at the same time and determines each SNP from a sample in which a plurality of targets are present in a mixed state.

EXAMPLE 1

Figure 3A:
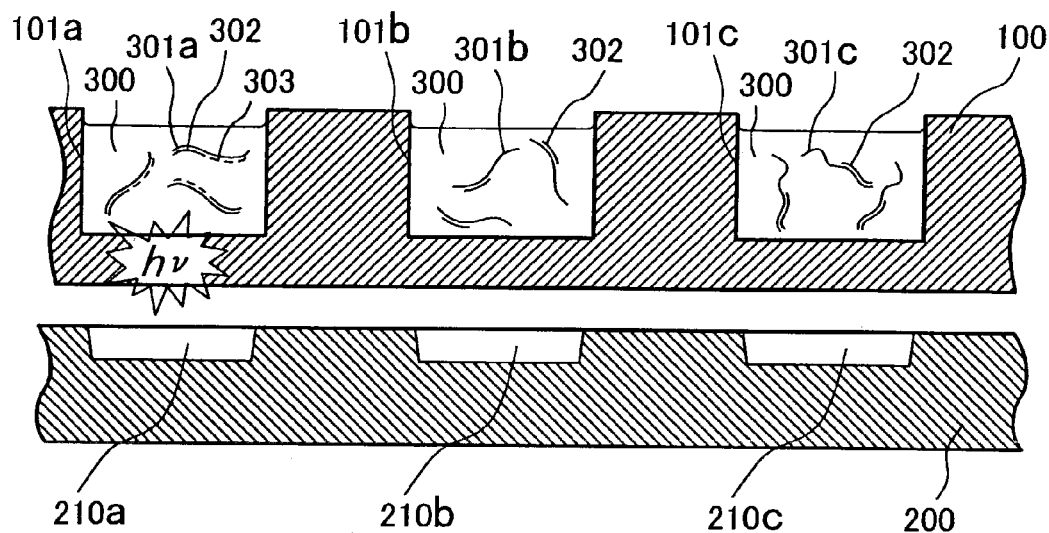
FIG. 3A is an illustration of a cross-section of a sample plate and a light-sensitive detector part in the apparatus detecting SNPs by chemiluminescence described in Example 1 of the present invention.
Figure 4A:
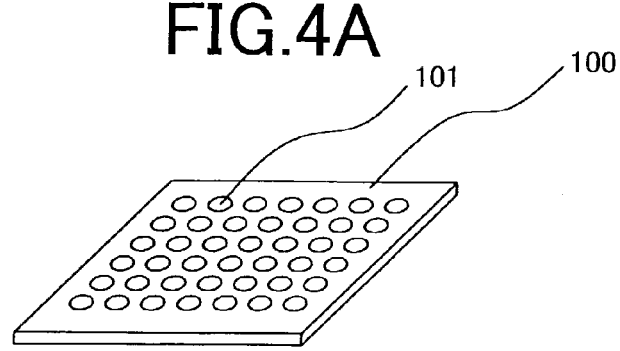
FIGS. 4A to 4C illustrate a package configuration of the optical sensor array and the sample plate according to the present invention.
Figure 4B:
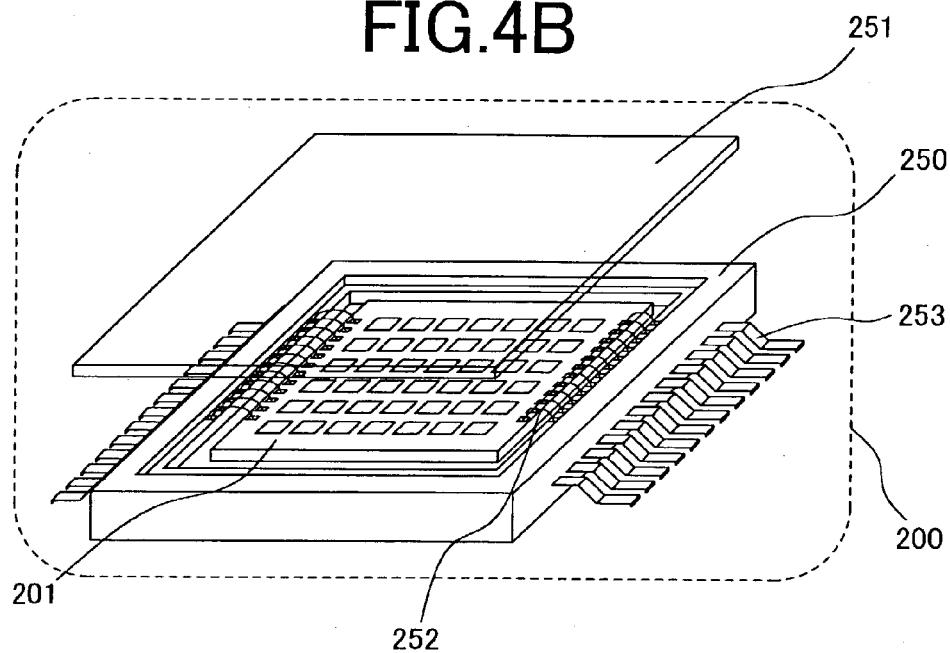
Figure 4C:
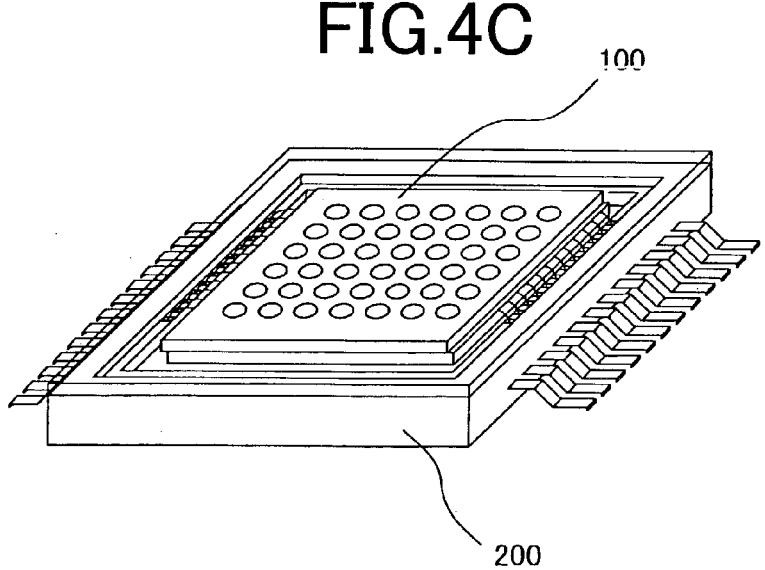
Figure 5A:
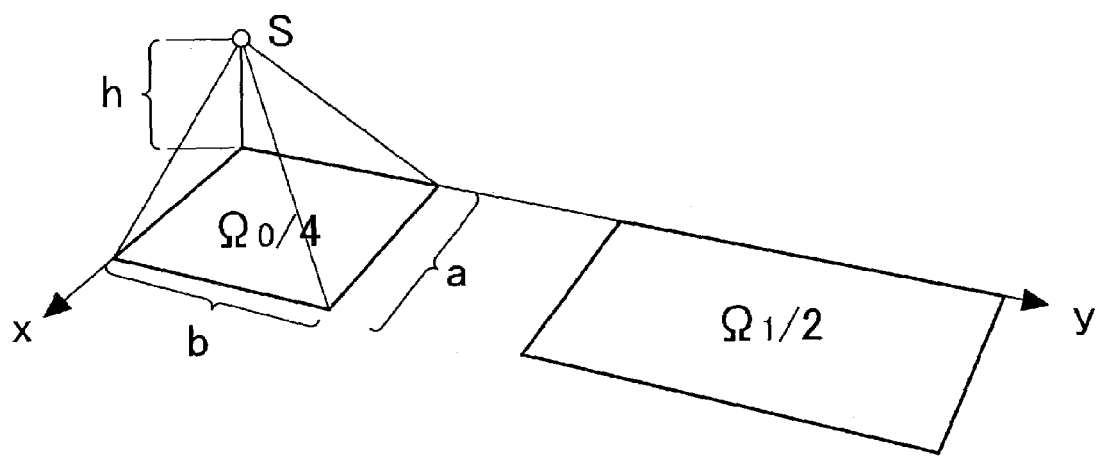
FIG. 5A is an illustration of a solid angle drawn over a photosensitive part with respect to a light source.

FIG. 3A is a cross-sectional view of a sample plate and optical sensor array illustrating an example of the present invention. A plurality of reaction baths and pixels are brought into a one-to-one correspondence and disposed in close proximity to each other. Here, a sample plate 100 comprises a plurality of reaction baths (2 mm in diameter, 2 mm in depth) 101a–c on a glass substrate. The bottom surface of the reaction baths is transparent, and a part of the light emitted from a sample arrives at an optical sensor array disposed underneath the sample plate. An optical sensor array 200 is composed of photodiodes 210a–c formed on a silicon substrate. Here, the positional relationship between the photodiodes and reaction baths is important. In conventional DNA assay apparatus, determination by fluorescence labelling is mainly utilized, and thus excitation light is required. Since the fluorescence, which is the signal, is faint in comparison with the intensity of the excitation light, it is necessary to provide a filter or spectroscopic device between the sample and light-sensitive detector in order to eliminate the influence of the excitation light. In contrast, in a detection system that utilizes chemiluminescence, an optical system to remove excitation light is not required and it is thus possible to minimize the distance between a sample and the detector. FIG. 4 shows an overview of a configuration that brings a sample plate 100 and a photodiode array 201 into close contact. As shown in FIG. 4B, photodiode array 201 is housed in a package 250 sealed by a transparent cap 251, and sample plate 100 is disposed in close contact with the transparent cap 251 (FIG. 4C). The intensity of light is attenuated inversely with the square of the distance from the light source, and thus the proportion of light of a reaction bath arriving at an adjacent pixel increases together with the distance between the sample plate and optical sensor. Thus, it is preferable that the distance between the photodiode array and sample plate be small. However, in reducing the distance it is necessary to take into account restrictions concerning the package housing for the photodiode array and electrostatic noise from the sample. An electrode pad on the photodiode array and a package pin 253 are connected by means of a wire bonding 252, and a space of approximately 1 mm is required to allow for dispersions in wire shape occurring in the bonding process. Electrostatic noise is caused by electrostatic coupling between a reaction solution 300 and a photodiode 210, and the strength of coupling increases in proportion to the square of the inverse of the distance. While this can be avoided by increasing the distance, a means is employed herein that lowers the noise of the photodiode by a shielding effect produced by forming a conductive film on the surface of the transparent cap 251 of the package 250 housing optical sensor array 251. Specifically, on a surface of transparent cap 251 of a thickness of 1 mm, an indium tin oxide (ITO) film of a thickness of 120–160 nm and resistivity of $2\times10^{-4}$ $\Omega$cm is vapor deposited at a substrate temperature of 300° C. a resistance heating vapor deposition device. By connecting this to ground potential when mounting the package of the optical sensor array to the apparatus, even if sample plate 100 is placed directly thereon noise caused by electrostatic coupling can be suppressed. As shown in FIG. 4B, in the packaging of photodiode array 201, the space of bonding wire 252, or the space between the photodiode array 201 and transparent cap 251, is necessary. With respect to these spaces, while it is necessary to maintain a certain amount of space from the viewpoint of component reliability and manufacturing yield, to ensure sensitivity and suppress crosstalk it is preferable that photodiode array 201 and transparent cap 251 be brought into as close proximity as possible. As shown in FIG. 5A, for a rectangular photosensitive part having the length and width dimensions of a and b, respectively, the steradlan drawn with respect to a point source S separated by a distance h from the vertex is represented by the following formula. (Hans Yurgen Henschel (REO Mori, translation), "Light and Illumination" NIHON RIKOUGAKU SHUPPANKAI (1994))

$$\Omega_{ab} = 4\sin^{-1}((ab/h^2)/(\sqrt{(1+(a/h)^2}\sqrt{(b/h)^2}))\Omega_0$$

$\Omega_0$: unit solid angle (=1 sr)

Figure 5B:
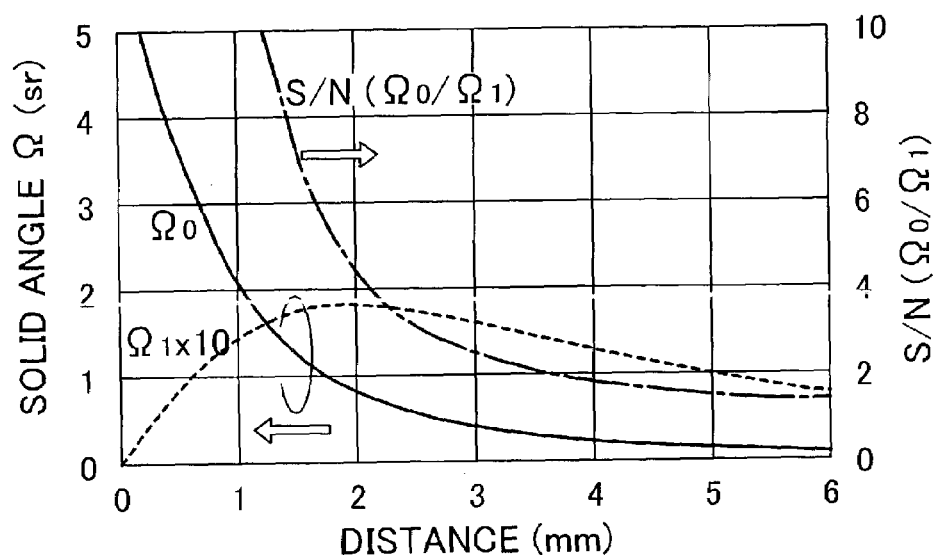
FIG. 5B is a diagram showing the relation between the distance between the photosensitive part and light source and the steradian, as well as the crosstalk relation.

FIG. 5B is a graph calculated using the above formula showing the relation between a solid angle $\Omega_0$ drawn over a square photodetector having a side of 2 mm and a solid angle $\Omega_1$ drawn over an adjacent photodetector (square having a side of 2 mm) disposed at an interval of 3 mm, which are directly below a light source, and a distance h. Here, light source S is located directly above the point of intersection of the diagonals of the photosensitive part, and a solid angle $\Omega_0/4$ drawn in the first quadrant of the x,y plane is calculated from symmetry and multiplied by 4. With respect to the adjacent photosensitive part, $\Omega_1/2$ is calculated from the symmetry to the y-axis and then multiplied by 2. When distance h is 1 mm, the solid angle $\Omega_0$ formed when light source S (corresponding to the center of a reaction bath) looks at photosensitive part (pixel) is approximately 2.1 sr, and the ratio of light reaching the pixel with respect to total radiation from an isotropic point source is 16.7% (=2.1/4$\pi$). Taking distance h as 3 mm, a solid angle subtended by a pixel is 0.4 sr, and the ratio of light reaching the pixel is 3.2% (=0.4/4$\pi$). From the viewpoint of realizing high sensitivity, it is not preferable to increase the distance between a sensor and sample more than this. As shown in FIG. 5B, a solid angle $\Omega_1$ (shown at tenfold magnification) drawn by an adjacent pixel with respect to light source S increases together with distance h, and after reaching a peak in the vicinity of 2 mm, it then decreases with h. Taking crosstalk with respect to light from an adjacent reaction bath as noise, the ratio with response to light from the reaction bath directly above is shown as S/N in FIG. 5B. When distance h exceeds 4 mm, S/N becomes smaller than 2, and a signal from the reaction bath directly above becomes twice or less that of a signal from an adjacent reaction bath. Therefore, a retaining mechanism of the sample plate is designed such that the distance between a pixel and the sample plate is 3 mm or less.

Figure 6A:
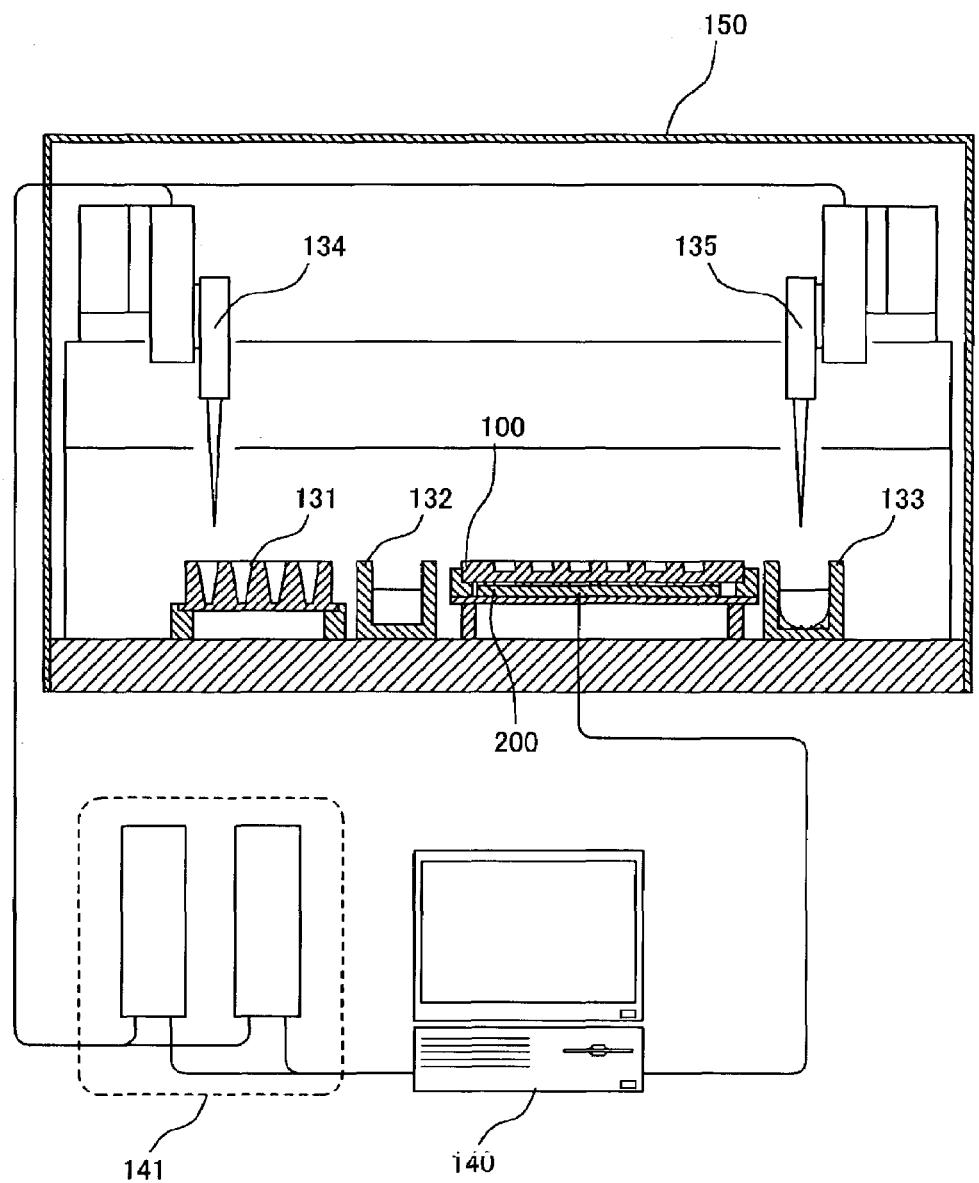
FIG. 6A is a drawing illustrating the configuration of an SNP analysis apparatus applying the method of locating an optical sensor array and sample plate according to the present invention.
Figure 6B:
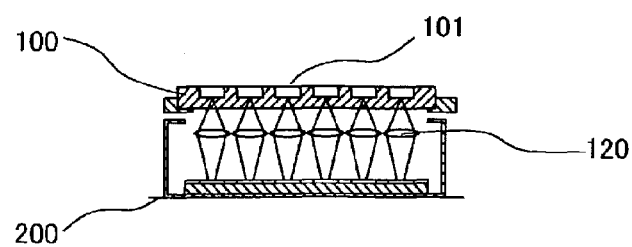
FIG. 6B is an illustration of a configuration combining the optical sensor array and sample plate according to the present invention by means of a condenser optical system.

FIG. 6A shows an example in which the configuration of a sample plate and optical sensor array for detecting light generated by chemical reaction according to the above constitution is applied to a detection apparatus. The shape of a photodiode photosensitive part was made as a 2 mm angle conforming to a reaction bath having a diameter of 2 mm. The respective pixels of the optical sensor array 200 and the reaction baths of sample plate 100 are fixed in a one-to-one correspondence, and the distance between them is set at 3 mm or less. A moving mechanism of a detector or sample plate 100 has been eliminated, enabling realization of a small-sized and low-cost apparatus. Further, since the distance between the detector and sample plate 100 is significantly decreased, enhanced detection sensitivity is enabled. FIG. 6B shows an example in which an optical system is inserted between sample plate 100 and optical sensor array 200 and fixed. By the addition of an optical system 120, in which pixels corresponding to light diffusing from the reaction baths are arranged, it is possible to decrease crosstalk to adjacent pixels while simultaneously enhancing optical coupling between the reaction bath and pixel.

EXAMPLE 2

Figure 3B:
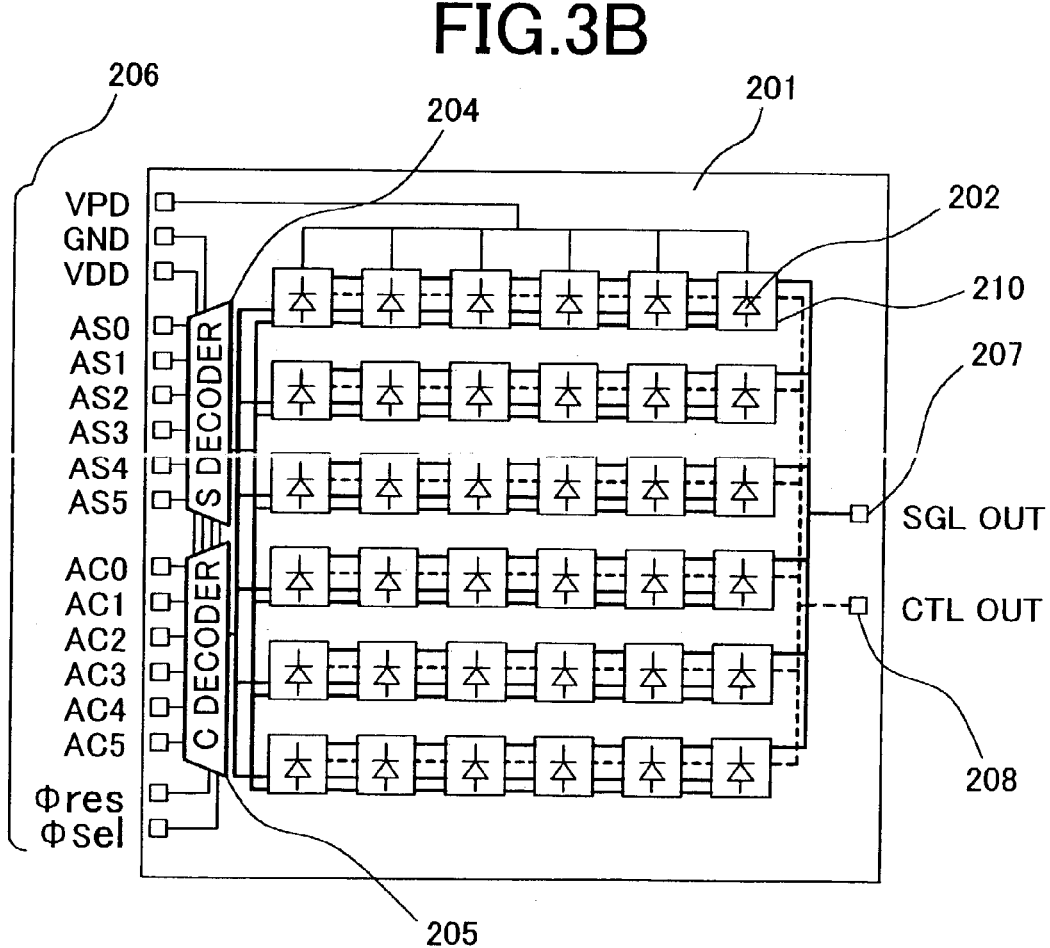
FIG. 3B is a block diagram illustrating the optical sensor array having 2 pixel addressing means described in Example 2 of the present invention.
Figure 7A:
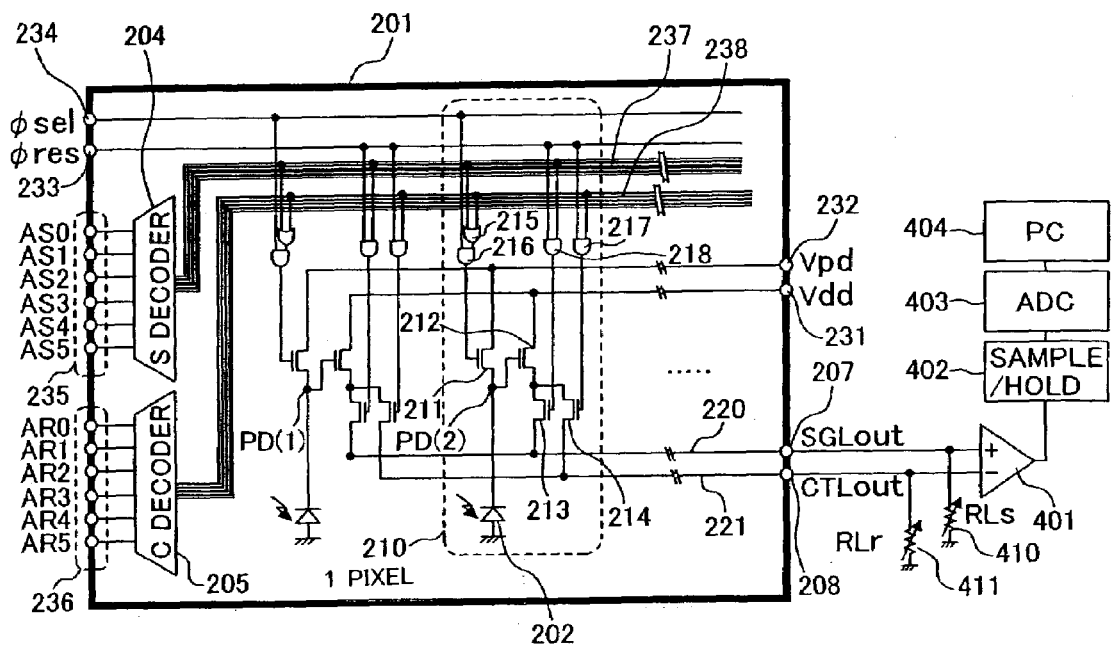
FIG. 7A shows a circuit diagram of the optical sensor array described in Example 2 of the present invention.
Figure 7B:
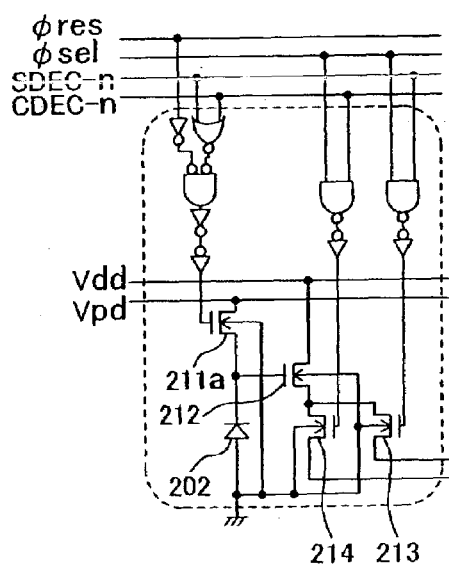
FIGS. 7B and 7C show the configuration of a pixel of the optical sensor array described in Example 2.
Figure 7C:
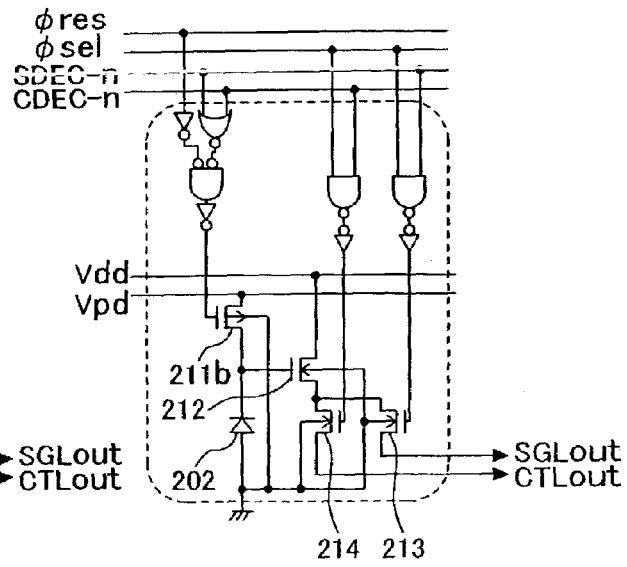

FIG. 3B shows a block diagram of an optical sensor array comprising 2 pixel-addressing circuits. FIGS. 7A to 7C show the circuitry diagram of the optical sensor array. Taking a photosensitive part 202 and a mechanism for resetting the photosensitive part and forwarding signals as 1 unit 210 (hereafter, referred to as "pixel"), a plurality of pixels is arranged on the same silicon substrate. The array shown in FIG. 3B comprises 36 pixels, wherein each pixel comprises a photodiode 202, a metal oxide semiconductor (hereafter, referred to as "MOS") transistor for reset 211, an MOS transistor for readout 212, and MOS transistors for pixel selection 213 and 214. Each pixel is independently selected by means of a decoder for target pixel selection (S-decoder) 204 or a decoder for control pixel selection (C-decoder) 205, and a signal is output to output terminals 207 and 208 corresponding to the respective decoders.

Conventionally, a shift register has been mainly used as a means for selecting a pixel and outputting a signal to an output terminal (IEEE J. Solid-state circuits vol. 9, 1 (1974)). A shift register generates a pixel selection signal in a sequentially fixed sequence and at a fixed time interval activated by trigger pulse. For an image sensor comprising many pixels advantages of a shift register include a reduction in control signals as well as a compact circuitry. While a shift register can also be applied in the present invention, an example is described herein in which a decoder that can randomly select a pixel is used (IEEE Transactions on electron devices vol. 38, 1772 (1991), IEEE Transactions on electron devices vol. 44, 1716 (1997)). In a sensor array for an analysis device, there is a need for flexibility in readout sequence, time interval setting and computation of the signal of each pixel, and these requirements can be met by applying a decoder. In a sensor array for use in analysis and assay, the number of pixels is comparatively small and the number of control signals and scale of a circuit does not become excessively large. A feature of the present example is that it comprises 2 decoders, enabling the selection of 2 pixels at the same time and differential amplification of the output thereof. Thus, fixed pattern noise inherent to each pixel, dark current, power supply fluctuations, and influence of background from the sample are excluded, enabling detection of signals at high sensitivity.

Figure 8:
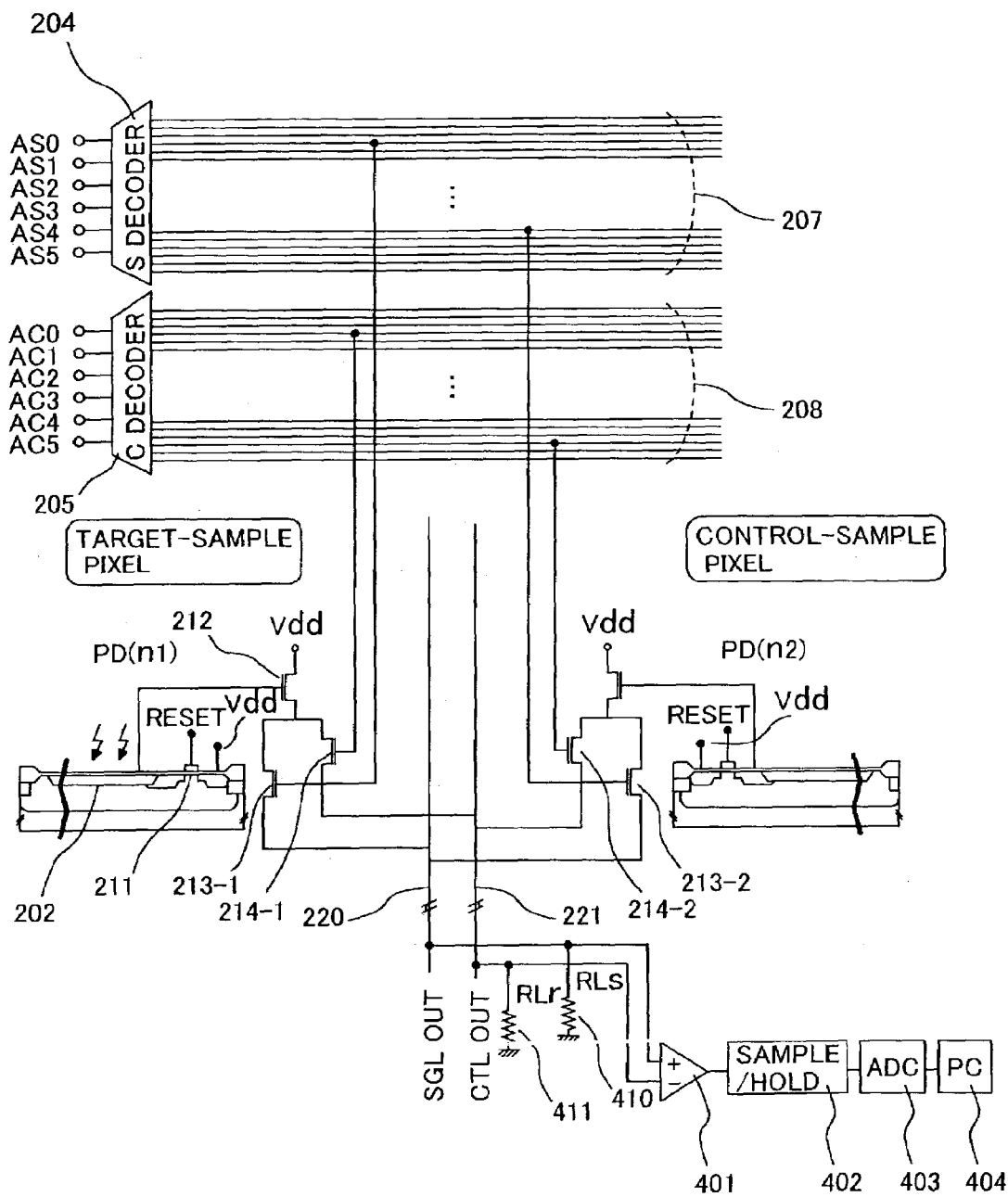
FIG. 8 is an illustration showing the path of a control signal that selects a target-sample pixel and control-sample pixel and the path or an output signal in the operation of the optical sensor array of Example 2 of the present invention.
Figure 9:
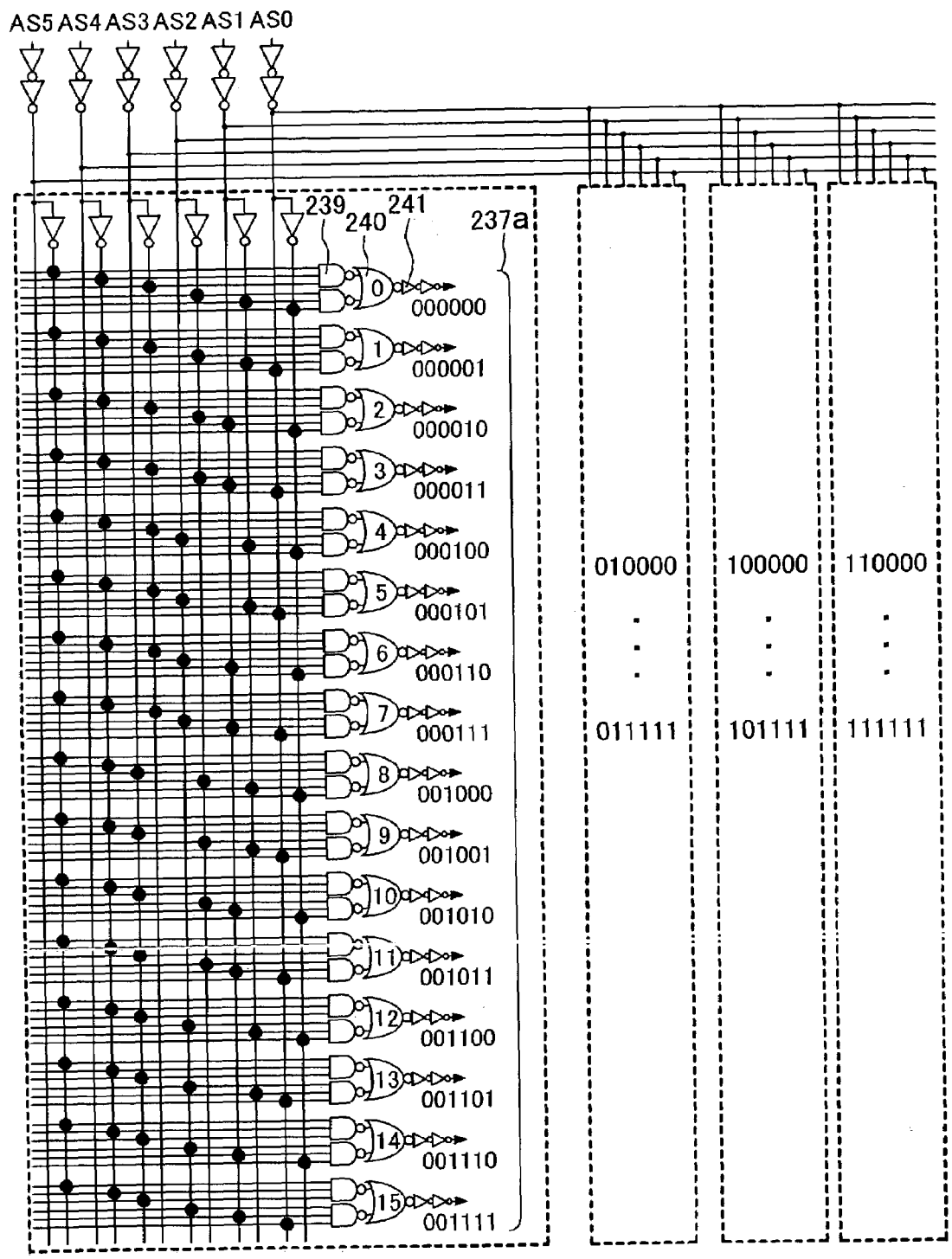
FIG. 9 shows the configuration of a decoder of the optical sensor array of Example 2 of the present invention.
Figure 10:
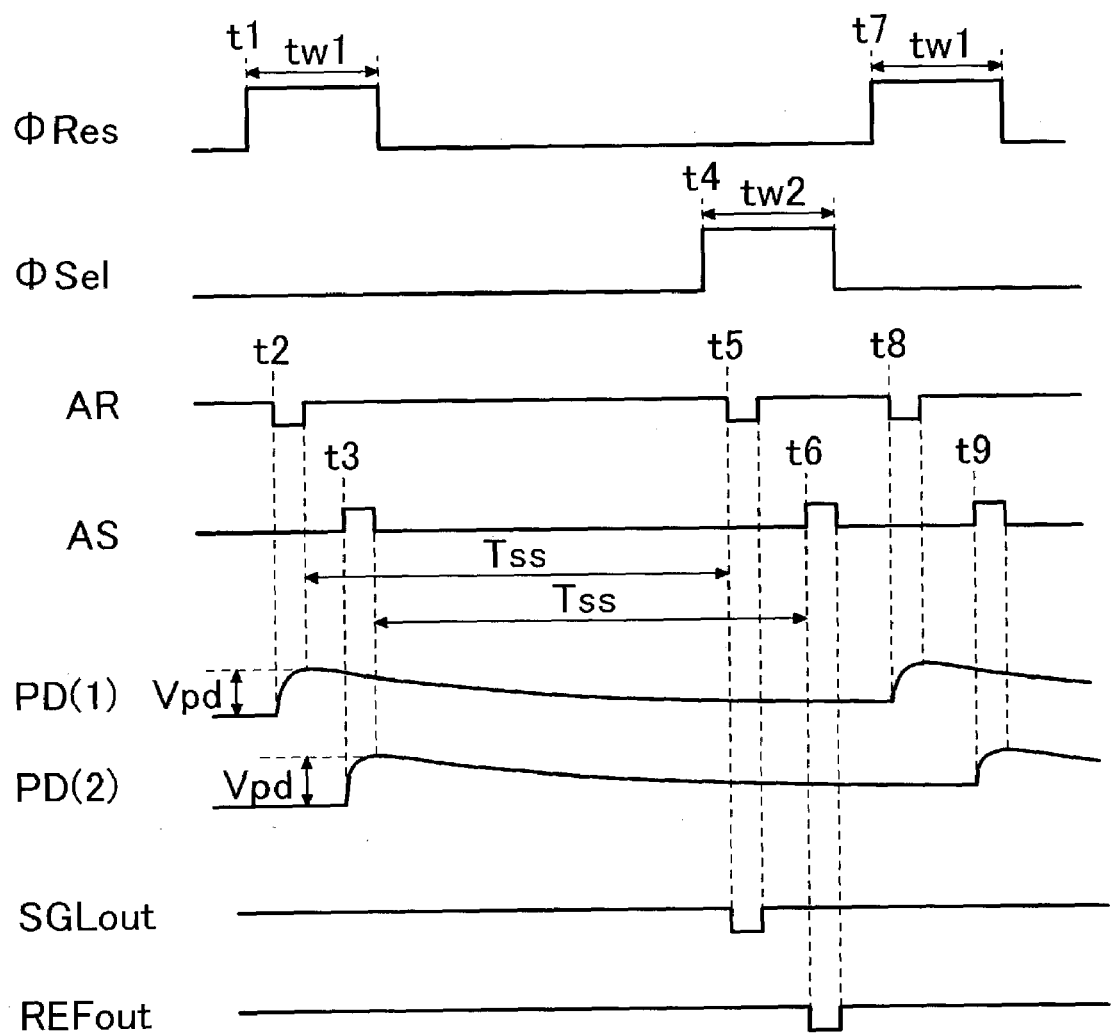
FIG. 10 is an illustration of a timing chart showing the operation of the optical sensor array described in Example 2 of the present invention.

FIG. 7A shows an example for the circuitry of the present invention. In order to randomly select 36 pixels, addresses of 6 bits each are imparted from AS0–5 235 and AR0–5 236 to an S-decoder 204 and a C-decoder 205, respectively. FIGS. 7B and 7C show the configuration of a pixel. FIG. 7B shows the configuration of a pixel using an n-channel MOS as a reset MOS, and FIG. 7C shows the configuration of a pixel using a p-channel MOS as a reset MOS. The following explanation concerns the former, and the latter will be explained in Example 4. Each pixel is constituted by a photodiode 202, and a reset MOS 211a, a readout MOS 212, and selection MOS 213 and 214 are n-channel MOS. FIG. 8 shows the paths selected by a target-sample pixel and control-sample pixel selected by decoders 204 and 205, through which the respective signals thereof are output. A pixel in which selection MOS 213-1 entered an ON state by means of S-decoder 204 becomes a target-sample pixel, and a pixel in which selection MOS 214-2 entered an ON state by means of C-decoder 205 becomes a control-sample pixel. All of the pixels comprise a selection MOS 213 connected to a target-sample signal output line SGLout 220 and a selection MOS 214 connected to a control-sample signal output line CTLout 221, and correspondence to a target-sample or control-sample can be freely set by means of output of the 2 decoders. FIG. 9 shows an example of one configuration of the S-decoder. A pixel can be randomly selected by means of a 6-bit address signal of AS0–5. While 64 pixels can be selected utilizing signals of 6 bits, in this case a part thereof is used for selecting 36 pixels. Here, 64 address spaces are split into 4 parts of 16 each, and decoding is carried out by means of a three-input NAND gate 239 and a two-input NOR gate 240. A signal 237a that selects a target-sample pixel is activated in buffer circuit 241 and sent to each pixel. A similar configuration as that shown in FIG. 8 can also be used for the C-decoder. FIG. 10 shows one example of an operation timing chart of the optical sensor array according to the present invention. For simplicity in explaining the timing, the number of pixels is taken as 2. In this case, the addresses of AS and AR each consist of 1 bit, and they select 2 pixels by "H" and "L". Resetting of the photodiode of each pixel and the readout timing are controlled by φsel and φres. Specifically, at the time of reset φres enters an ON state (taken as "H") and φsel enters an OFF state (taken as "L"), and a photodiode selected by S-decoder or C-decoder in accordance with address AS and AR is charged (reset) up to a preselected voltage Vpd by way of the reset MOS 211. When address AS and AR become unselected, the photodiode enters a charge storage mode and begins to capture and accumulate signal light from a sample. As shown in FIG. 10, with the passage of time the potential of a node PD(1) or PD(2) starts to decline from reset potential Vpd in accordance with the quantity of light taken in. After a signal storage time Tss, φres becomes "L" and φsel becomes "H," and when a pixel is by AS and AR the device enters signal read mode. By means of MOS for selection 213 and 214 that are provided in each pixel and connected to S-decoder and C-decoder, the signal of a pixel, that is, the potential of nodes PD(n1) and PD(n2), is output to common output lines SGLout 220 and CTLout 221. By reading the amount of voltage decrease of nodes PD(n1) and PD(n2) in this manner, the amount of light can be determined.

An example of fabrication of each device comprising a pixel will now be described. A p–n junction is formed on a silicon substrate (p-type, resistivity 10 Ωcm) by means of an n-type diffusion layer and employed as a photodiode. The shape of the n-type layer to be the light-receiving surface is 2 mm square in conformity with the size of a reaction bath (diameter 2 mm). For the n-type MOS transistor for reset 211, a source electrode is connected to a cathode (n-type) of a photodiode, a drain is connected to the above-mentioned Vpd, and Vpd is set at 2.6 V. Gate width/gate length (W/L) is set at 1200 μm/0.6 μm such that a charge time (reset time) of a photodiode is 10 μs or less. The design size of the n-type MOS transistor 212 that comprises a source follower to read out the cathode potential of a photodiode is W/L=4000 μm/2.0 μm, where, for W, conductance is made high to lower thermal noise, and L is designed larger than the minimum design rule to facilitate lowering of 1/f noise. For n-type MOS transistors for pixel selection 213 and 214, W/L=100 μm/0.6 μm so that a parasitic resistance effect does not occur in the source follower circuit.

As another example, it is possible to realize more advanced functions by having the apparatus comprise more than 2 decoders, and simultaneously selecting more than 2 pixels and performing computation, averaging and noise processing therefor.

EXAMPLE 3

Figure 11A:
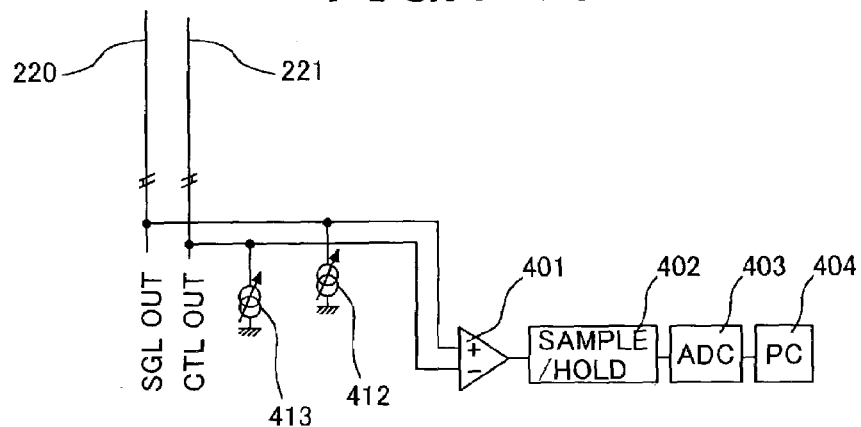
FIGS. 11A to 11C illustrate a circuit that actively controls the current source or load resistance of a source follower circuit of the optical sensor array described in Example 3 of the present invention.

FIG. 11A shows an example of the configuration of a part in which a signal is output by way of output lines 220 and 221 corresponding to the decoder for selection of a target pixel (S-decoder) 204 and the decoder for selection of a control pixel. Current sources 412 and 413 are connected to output line for a target pixel signal 220 and output line for a control pixel signal 221, respectively, and, for example, current is initially set to 2 mA. The two output lines are connected to an input terminal of a differential amplifier 401, the output of the differential amplifier is connected to a sample/hold circuit, and the output thereof is read into a control computer 404 via an AD converter 403. Prior to measuring luminescence from a target sample, a target-sample and control-sample are measured at the same time in a state where the target-sample is not allowed to emit luminescence, for example in a state where luciferin, the luminescence substrate, is not added thereto, and the set values of current sources 412 and 413 is corrected such that the difference in output between the two samples becomes 1 mV or less. By means of this correction, even if a gain of the differential amplifier is 1000, the differential output in a dark state is 1 V or less and linearity of output with respect to input can be maintained without saturation of output. As a result, dispersal of MOS transistor characteristics and noise caused by differences in wiring resistance, which are unavoidable in production, can be eliminated, enabling differential amplification at a high amplification power, thus making possible the detection of a minute signal.

Figure 11B:
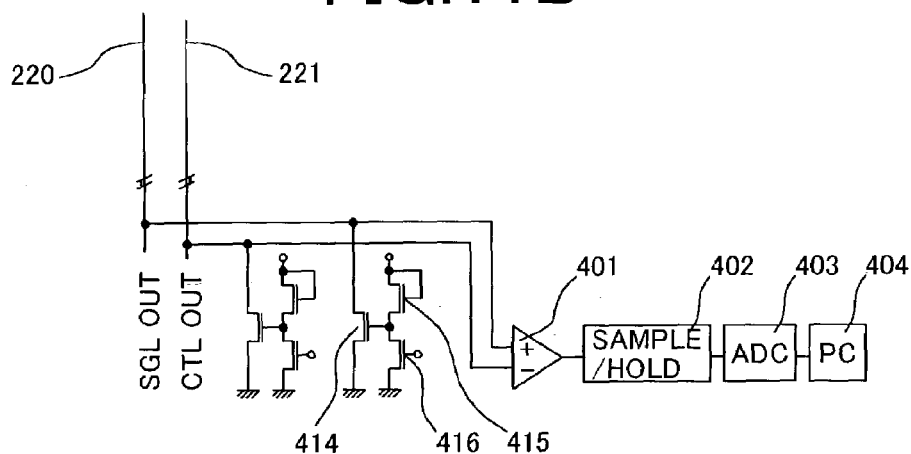
Figure 11C:
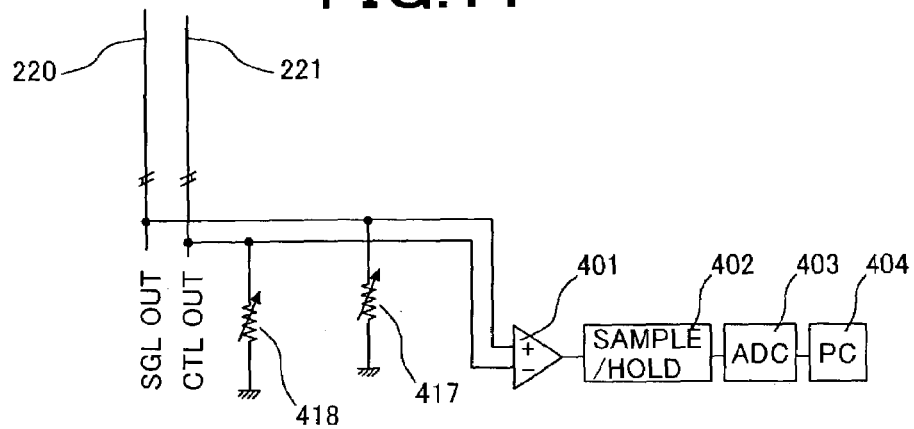

FIG. 11B shows one example of the configuration of a current source. MOS transistors 415 and 416 are connected between a apply voltage and ground voltage, and the gate of 415 is connected to its drain to operate as a diode, and by adjustment of the gate potential of 416 conductance is made variable. A gate of MOS transistor 414 is connected to the junction point of 415 and 416. Here, by varying the gate potential of MOS transistor 416, current flowing to MOS transistor 414, the current source, is varied, to perform offset correction. Another method is shown in FIG. 11C. Here, as load resistance of a source follower, electrically variable potentiometers 417 and 418 (for example, AD8403 manufactured by Analog Devices Ltd.), which can change resistance value by means of a signal imparted thereto, are used. In the above-described correction operation the signal of each pixel in a dark state is recorded, and the value of the above potentiometers is adjusted for each pixel such that the output in a dark state of all pixels is constant, and adjustment is carried out such that output of the differential amplifier in a state prior to infusion of a reagent to begin emission of luminescence from a sample is zero.

Next, an example is illustrated of chemiluminescence determination by a detection apparatus in which the optical sensor array of FIG. 7A and the current source of FIG. 11C are applied. Here, as represented by the following reaction formula, a system is used in which luciferin is oxidized in the presence of ATP and luciferase to emit light.

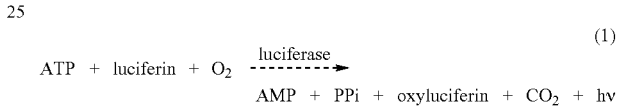

$$\text{ATP} + \text{luciferin} + O_2 \xrightarrow{\text{luciferase}} \text{AMP} + \text{PPi} + \text{oxyluciferin} + CO_2 + h\nu \quad (1)$$

Figure 12:
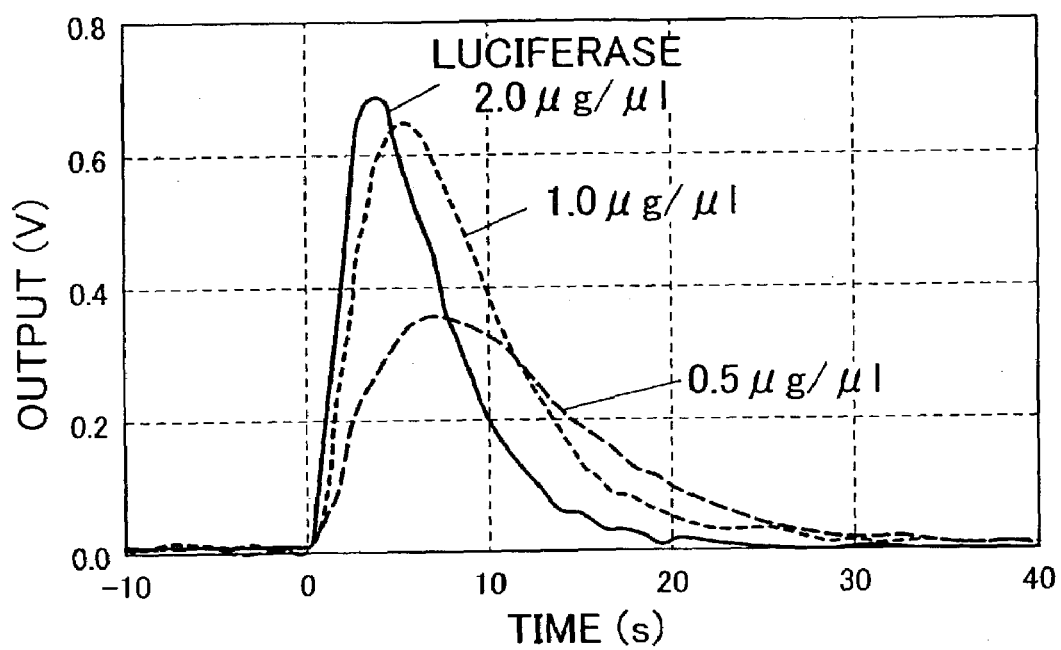
FIG. 12 is a diagram showing time-variation data for chemiluminescence measured by the apparatus and method for luminometric assay according to the present invention.

Specifically, a base solution is used in which luciferin (0.1 μg/μL) and luciferase (0.5, 1.0 and 2.0 μg/μL) are dissolved in a buffer (10 mM Tris-acetate buffer, pH 7.75) and an ATP solution ($2 \times 10^{-7}$ M, 0.05 μL) is added thereto. FIG. 12 shows the change over time in chemiluminescence. By the addition of ATP, luminescence is observable in accordance with the above reaction formula. Taking the signal storage time Tss as 1 second, luciferase concentration-dependency can be obtained by observing the change in luminescence over time.

EXAMPLE 4

By employing a p-channel type MOS as MOS transistor 211 for resetting the photodiode shown in FIG. 7A, the reset time can be speeded up. In the case of using n-channel type MOS transistor 211a, as in FIG. 7B, as the photodiode is charged and the circuital node PD(2) approaches Vpd, by an effect whereby the source is biased in a reverse direction to the silicon substrate, the threshold voltage of the reset MOS transistor increases and the ON resistance of the MOS rises. As a result, a time constant for charging the photodiode to specified potential Vpd increases. As shown in FIG. 7C, by employing a p-channel MOS type transistor 211b, the substrate bias effect can be eliminated to enable reset at high speed.

EXAMPLE 5

Figure 13A:
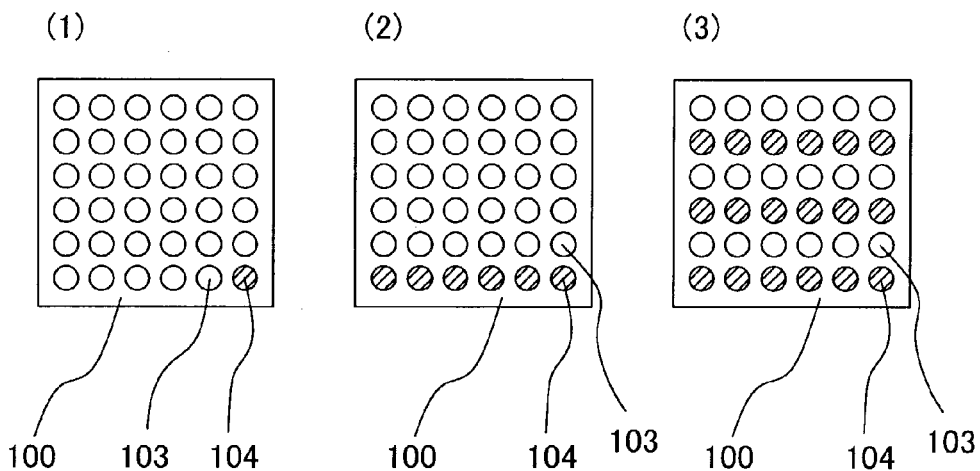
FIG. 13A is a diagram showing an example of the arrangement of a sample plate and target samples and control samples used by the SNP assay apparatus described in Example 5 of the present invention.
Figure 13B:
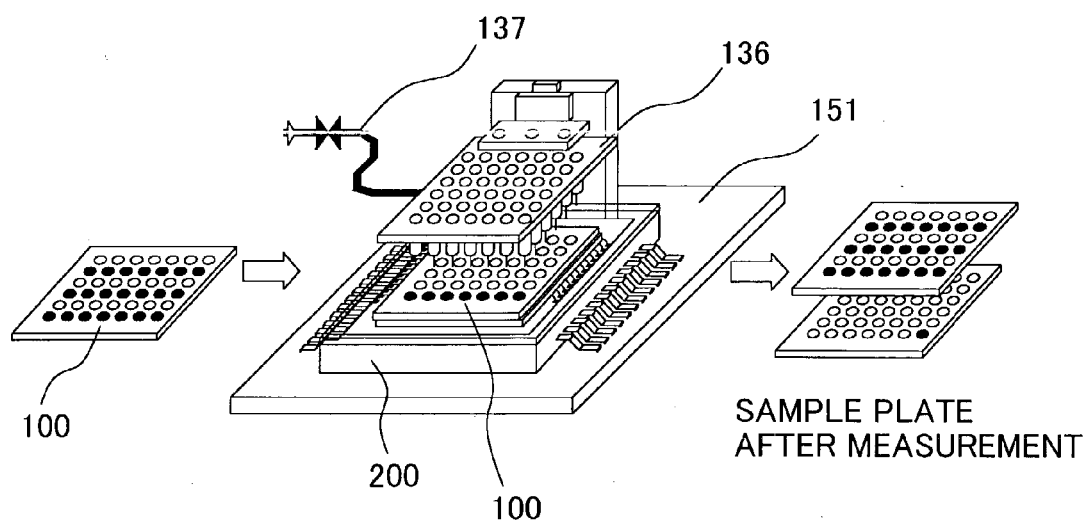
FIG. 13B illustrates a configuration that combines the optical sensor array, sample plate and reagent dispenser described in Example 5 of the present invention.

FIGS. 13A and 13B are an illustration of an example of determination by an assay apparatus applying the present invention. FIG. 13A (1–3) illustrate a method of inserting various types of samples into a sample plate 100 comprising 36 reaction baths. Target samples for typing of SNPs are inserted into reaction baths 103, shown as white in the figure, and a control sample is inserted into reaction bath 104, shown by shading in the figure. In determining various samples, it is necessary to perform offset correction according to the characteristics of the samples and reagents. For samples having a signal of a comparatively strong intensity or samples having weak background light, many samples can be assayed at the same time by using one common control sample on each sample plate, as shown in FIG. 13A (1). In a case of differing detection items, especially in a case when the level of background light differs for each detection item, offset correction is performed by providing one control sample for six types of detection items, as shown in FIG. 13A (2). For a sample having a particularly weak signal and consequently sensitive to measurement conditions, as shown in FIG. 13A (3), by placing a control sample in a position adjacent to the reaction bath of the target sample and performing offset correction, measurement at high sensitivity is enabled. According to the present invention, to allow flexible selection or a target sample and control sample, as shown in FIG. 13B, effective offset correction is realized for a variety of samples and measurement items, thus enabling an increase in throughput while maintaining high measurement accuracy.

Figure 14:
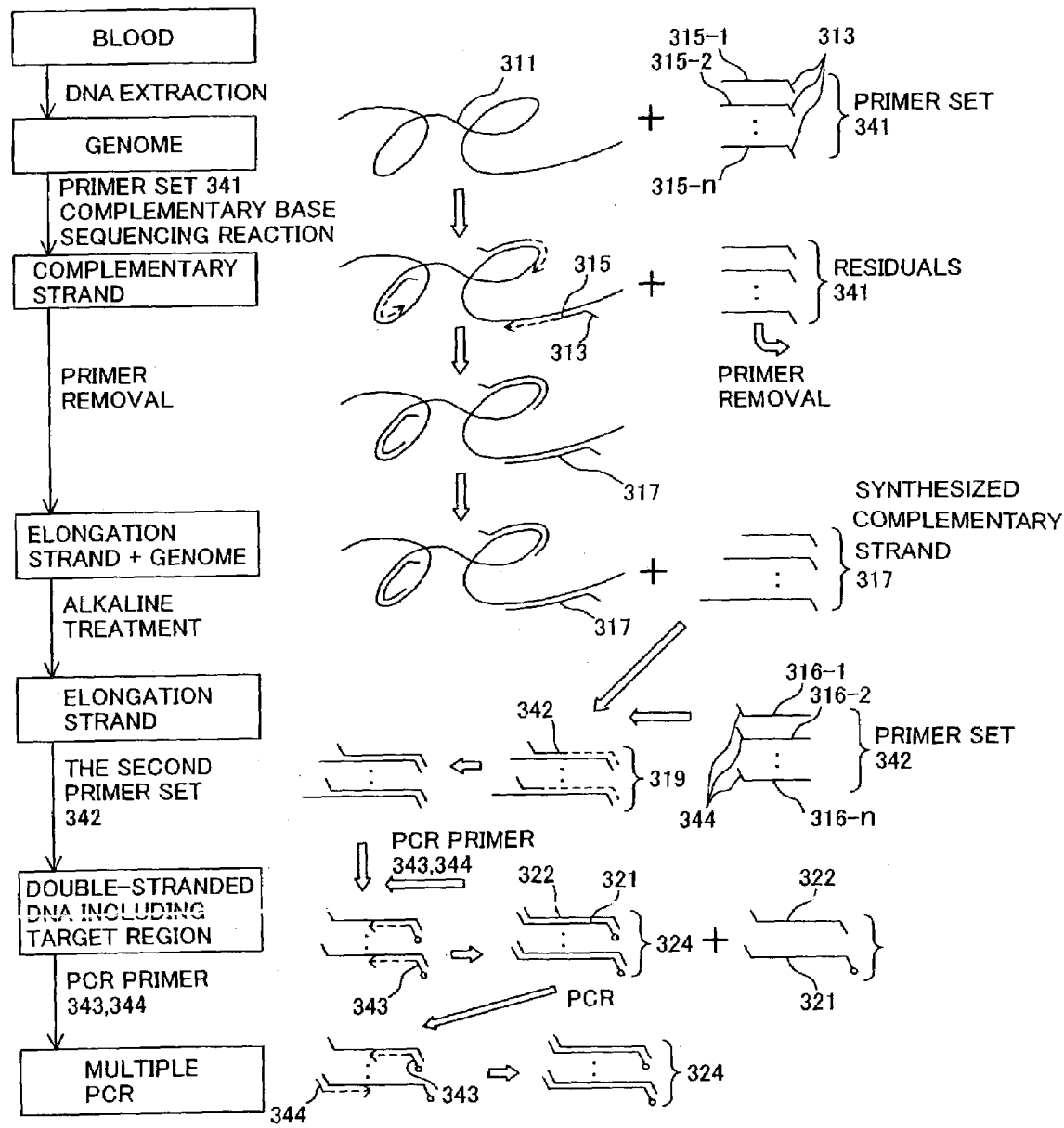
FIG. 14 shows the flow of procedures in extracting a DNA sample from blood described in Example 5 of the present invention.

The present invention relates to a genetic testing system or DNA system. Accordingly, the process of preparation of a sample to be utilized therein will now be described in a concrete manner. However, a sample preparation method is not limited to the method described herein. FIG. 14 shows a process from extraction of genome from blood to PCR amplification of a plurality of target regions that are the object of assay. After target DNA is obtained, DNA testing is carried out according to the procedure shown in FIG. 2.

Initially, genome DNA is isolated from blood. To achieve this, a commercially available DNA extractor or extraction reagent kit or the like is used. First, 18 mL of 50 mM NaCl solution is added to 2 mL of whole blood to hemolyze erythrocytes. The resulting solution is centrifuged for 15 min at 3500 rpm at 4° C. to obtain precipitate. The obtained precipitate is washed with 50 mM NaCl solution, and the differential count of leukocytes is obtained. One mL of DNAzol (GBCO BRL) is added thereto, to lyse cell walls. The solution is drawn in and out with a syringe having an 18 G injection needle to cut genome DNA into short segments, and then centrifuged to remove unwanted substances. After adding 0.5 mL of ethanol and stirring, the solution is centrifuged to recover genome DNA. After rinsing with 70% ethanol, 400 μL of water is added thereto and lysing is conducted at 65° C. Eight μL of 10 mg/mL RNase A is then added thereto, and the resulting solution is incubated at 37° C. for 2 hours to decompose RNA. 400 μL of a mixed solution of phenol, chloroform and amyl alcohol is added thereto to deactivate enzyme. Genome DNA is then recovered by a propanol precipitation operation, and lysed in 200 μL of 0.5×TE (pH 8.0). About 100 μg/mL of genome DNA solution is obtained by this operation. Multiple PCR may also be performed with genome as a target, using extracted genome DNA 311 as template and with a PCR primer provided at each site to be determination. However, as differences in the sequences of primers causes differences in hybridization efficiency, simultaneously amplifying various types of DNA by PCR frequently involves difficulty. Here, a method is employed by which multiple PCR can be reliably conducted, however a different method may also be used. A primer set 341 having an anchor sequence on the 5'-side of various DNA sites that are the objects of interest is hybridized to genome DNA 311 to carry out complementary strand synthesis. Primer set 341 comprises a set of primers having a common anchor sequence 313 at the 5'-terminus, and having sequences 315-1, 315-2 . . . 315-n that differ for each SNP of interest on the 3'-terminal side of common anchor sequence 313. Specifically, to 1 μL of genome DNA sample was added 5 μL of 10×PCR buffer solution attached to HotStarTaq (Qiagen), 2 μL of 5 mM dNTP, 5 μL of primer 341 (1 pmol/μL), 37 μL of water and 0.25 μL of HotStarTaq, and after heating the resulting mixture at 95° C. for 10 min, the steps of heating at 57° C. for 30 sec and 72° C. for 60 sec were repeated 5 times to amplify specific DNA regions. Primers 341 have a sequence that is specific to each object of interest, which will be a target, and have common anchor sequence 313 at the 5'-terminus. After complementary strand synthesis, residual primers are removed in order to prevent primers reacting amongst themselves to produce unwanted DNA products. A spin column (Ultrafree C3, manufactured by Millipore) having an ultrafiltration membrane with a molecular weight cut-off of 100000 Dalton was used as the method of removal. 50 μL of reaction sample solution was placed on the spin column and centrifuged at 3000 g for 3 min. 100 μL of buffer solution of 10 mM Tris-HCl (pH 8.0) and 1 mM EDTA was then added thereto and the resulting solution was centrifuged in the same manner. The ultrafiltration membrane was rinsed well with 50 μL of the same buffer solution, to recover genome DNA 311 and a complementary strand 317 remaining on the ultrafiltration membrane. Since the DNA strand 317 that underwent complementary strand extension is in a state of being hybridized to genome 311 it is possible to recover it by ultrafiltration together with the genome. Complementary strand 317 is then liberated by increasing the temperature. Primers 342 are then hybridized thereto so as to sandwich a site to be determined, and complementary strand synthesis is carried out using HotStarTaq under the same reaction conditions as described above.

Alternatively, complementary strand 317 may be recovered by labelling the 5'-terminus of primers 341 with biotin beforehand, and after synthesis of complementary strand 317, separating double-stranded DNA strands obtained by complementary strand synthesis using magnetic beads with avidin by utilizing biotin-avidin bonding. Specifically, to 1 μL of genome DNA 311 sample prepared above, add 5 μL of 10×PCR buffer solution attached to HotStarTaq (Qiagen), 2 μL of 5 mM dNTP, 5 μL of biotinylated primers 341 (1 pmol/μL), 37 μL of water and 0.25 μL of HotStarTaq. After heating the resulting mixture at 95° C. for 10 min, repeat the steps of heating at 94° C. for 30 sec, 57° C. for 30 sec and 72° C. for 60 sec 5 times to amplify specific DNA regions. To the PCR product (200–500 fmol), add 1 μL of Dynabeads (M280) Streptavidin (Dynal, $6.7 \times 10^8$ beads/mL), which are magnetic beads, and 25 μL of a solution of 2 M NaCl, 1 mM EDTA, 0.02% NP-40, and 10 mM Tris-HCl (pH 7.5), and stir at 25° C. for 30 min. Using a magnet, recover double-stranded DNA 311 and 317 obtained by complementary strand synthesis.

To the recovered complementary strands 317, add a primer set 342 comprising a set of primers having an anchor sequence 344 at the 5'-terminus, and having sequences 316-1, 316-2 . . . 316-n that differ for each object of interest on the 3'-terminal side of common anchor sequence 344, and carry out complementary strand synthesis. As a result, double-stranded DNA having a region that is an object of interest is obtained. A solution of double-stranded DNA obtained in this way from the double-strands includes DNA strands corresponding to all DNA regions of interest. Next, simultaneously add common primers 343 and 344 thereto and conduct PCR amplification. The 2 primers 343 and 344 used in PCR amplification are common for all double-stranded DNA fragments 324, and therefore there are no differences in DNA strand amplification due to differences in hybridization efficiency of the primers. Thus, the DNA of all regions of interest is uniformly amplified. The following conditions are used for PCR reaction. To 1 µL of double-stranded DNA solution prepared above, add 5 µL of 10×PCR buffer solution attached to HotStarTaq (Qiagen), 2 µL of 5 mM dNTP, 5 µL of the two types of primers for PCR (1 pmol/µL), 37 µL of water and 0.25 µL of HotStarTaq. After heating the resulting mixture at 95° C. for 10 min, repeat steps of heating at 94° C. for 30 sec, 57° C. for 30 sec and 72° C. for 60 sec 30 times to amplify all the DNA regions of interest. At this point, primer 343 is labeled with biotin, and, using magnetic beads, all double-stranded DNA 324 comprising DNA sequences as targets are recovered. They are then formed into a single strand, and used as target DNA. There are two ways for forming a single strand: one using DNA strands with biotin attached, and the other using the complementary strands thereof. A method for forming a single strand using magnetic beads is as follows. Recover magnetic beads bonded with PCR product containing biotin residue using a magnet, suspend the beads in 100 µL of 0.1 M NaOH, and after allowing to stand for 5 min, wash with water to obtain single-stranded DNA immobilized on beads or single-stranded DNA released in NaOH solution. Suspend single-stranded DNA immobilized on beads in 10 µL of water and use as a sample. In the case of single-stranded DNA released in NaOH solution, immediately neutralize with 3M acetic acid, precipitate with ethanol, and then dissolve in 10 µL of water for use as a sample. It is also possible to use a single strand comprising a DNA sequence of interest produced by asymmetric PCR in which the concentration of primer 343 is made relatively higher than that of primer 344. In this case, it is necessary to remove inorganic pyrophosphate, a hindrance to chemiluminescence detection, and to use dATP-αS in place of dATP as the substrate for reaction with luciferin. In this way, various DNA strands of interest are obtained as single strands in a reaction tube.

An example will now be described of assay by means of BAMPER of the target DNA obtained above using a configuration of the sample plate and optical sensor according to the present invention. A difficulty in detecting SNPs lies in the fact that in order to investigate a difference of a single nucleotide in a nucleotide sequence, it is not possible to use simple hybridization assay using a DNA chip or DNA length analysis by standard gel electrophoresis. A feature of the BAMPER technique is that the 3'-terminus of a primer is designed so as to come to a position at which it attempts to detect a mutation, and synthesis of the complementary strand is then carried out. Complementary strand extension of the primer depends significantly on whether or not its 3'-terminus matches with the target. If they match, complementary strand extension occurs, but if they do not match complementary strand extension rarely occurs. Utilizing this point, the identification of SNPs can be performed. However, there are cases in which complementary strand synthesis proceeds even when terminal nucleotides are in a mismatched condition. In order to prevent this an artificially mismatched nucleotide is inserted near the 3'-terminus of the primer. In this case, when a mismatch already exists at the terminus of the primer it results in the existence of 2 mismatches in the terminal region of the primer and complementary strand extension of the primer can hardly ever occur. On the other hand, when the 3'-terminus matches with the target, even though an artificial mismatch is present near the terminus, complementary strand synthesis occurs and inorganic pyrophosphate is released. By inserting an artificial mismatch near the 3'-terminus of the primer it is possible to perform accurate control of complementary strand synthesis by means of match or mismatch of the primer terminus. The reaction formula is as follows.

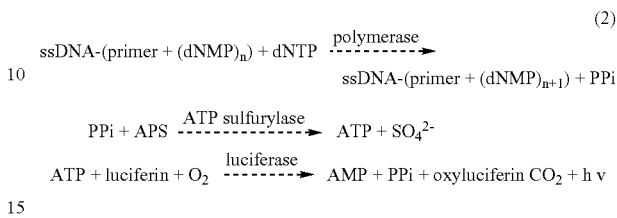

(2)

Figure 1:
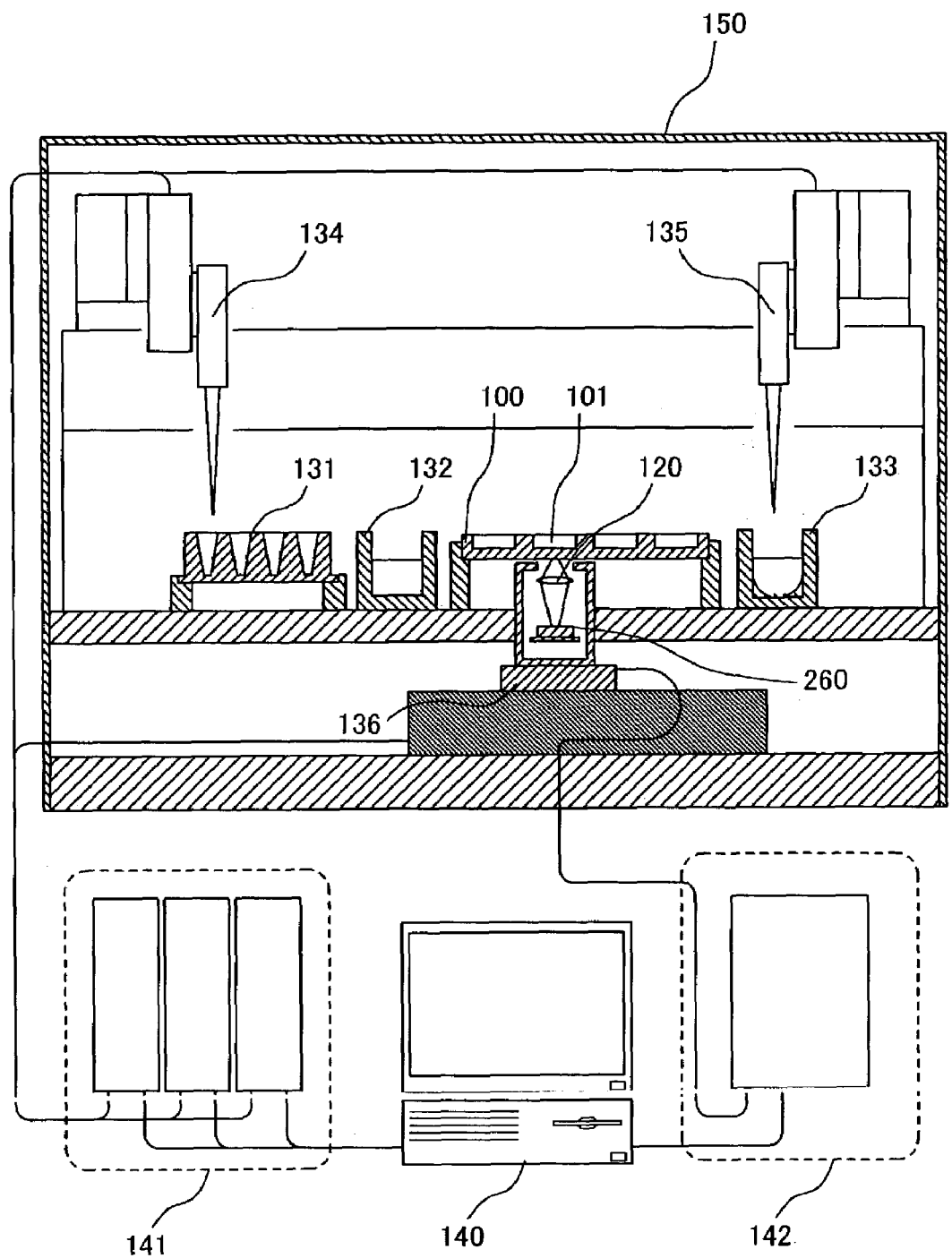
FIG. 1 is an illustration of a genetic testing device according to a conventional example.
Figure 2:
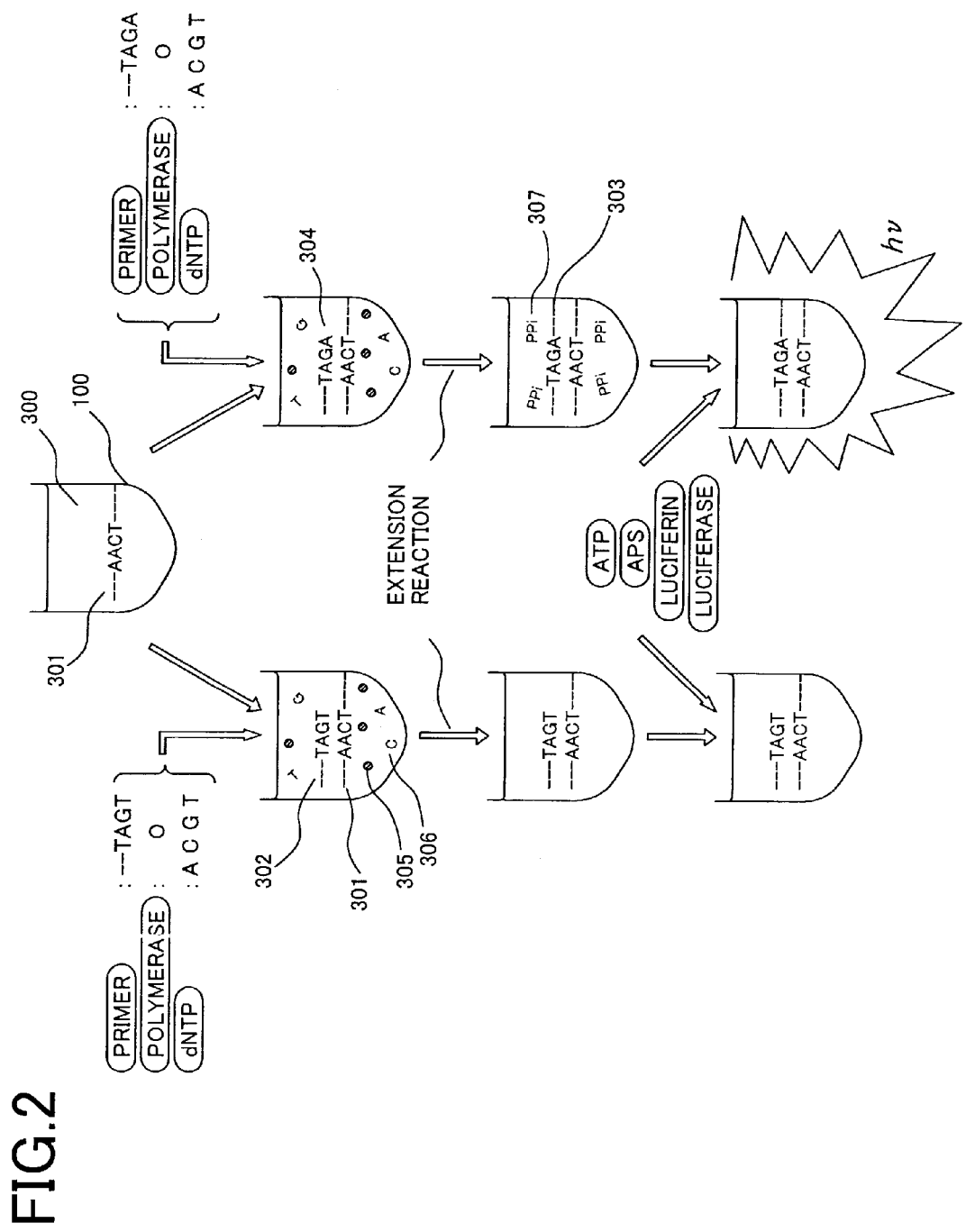
FIG. 2 shows the flow of protocol of the BAMPER technique, which is one of the SNP detection techniques used by the present invention.

As shown in FIG. 2, by DNA complementary strand synthesis of reaction substrate dNTP (deoxynucleotide triphosphate) 306 in the presence of DNA polymerase 305, inorganic pyrophosphate (PPi) 307 is produced as a byproduct. When this is reacted in the presence of APS (adenosine5-phosphosulfate) and ATP sulfurylase, ATP is generated. ATP reacts in the presence of luciferin and luciferase to emit light, and by determining the light, complementary strand extension 303 is detected. Since PPi is generated in the luminescence reaction, luminescence is maintained by consuming ATP.

The reagents and composition used in this technique are as follows.

(i) Reaction Solution
   0.1 M Tris-acetate buffer, pH 7.75
   0.5 mM EDTA
   5 mM magnesium acetate
   0.1% bovine serum albumin
   1 mM dithiothreitol
   0.2 mg/mL polyvinylpyrrolidone
   0.2 U/µL DNA polymerase I, Exo-klenow Fragment
   1.0 U/mL ATP sulfurylase
   2 mg/mL luciferase (ii) Base Solution A
   10 mM Tris-acetate buffer, pH 7.75
   25 µM dNTPs
   1.0 µM APS (iii) Base Solution B
   10 mM Tris-acetate buffer, pH 7.75
   20 mM D-luciferin The procedures of BAMPER assay using a synthesized oligonucleotide (the same sequence as p53) as a DNA sample will now be described. A mutation site in the p53 sequence is underlined. DNA samples and primers for genome typing used as examples are shown below (all purchased from Amersham Pharmacia Biotech). In addition, artificially mismatched primers were used as the primers for genome typing.

```
[p53exon 8-wild type]
5'-CTTTC TTGCG GAGAT TCTCT TCCTC TGTGC GCCGG TCTCT
CCCAG GACAG GCACA AACAC GCACC TCAAA GCTGT TCCGT
CCCAG TAGAT TACCA-3'

[p53exon 8-mutant type]
5'-CTTTC TTGCG GAGAT TCTCT TCCTC TGTGC GCCGG TCTCT
CCCAG GACAG GCACT AACAC GCACC TCAAA GCTGT TCCGT
CCCAG TAGAT TACCA-3'

[primer for genome typing (for wild type)]
```

```
                -continued
5'-AACAGCTTTGAGGTGCGTGATT-3'

[primer for genome typing (for mutant)]
5'-AACAGCTTTGAGGTGCGTGATA-3'
```

To DNA sample 301 as a target (10–100 fmol/μL) was hybridized a 1.5-fold amount of a probe (primer) for genome typing 302 in an annealing buffer (10 mM Tris-acetate buffer, pH 7.75, 2 mM magnesium acetate) (94° C. for 20 sec→65° C. for 120 sec→room temperature), to obtain a DNA sample solution.

Figure 15A:
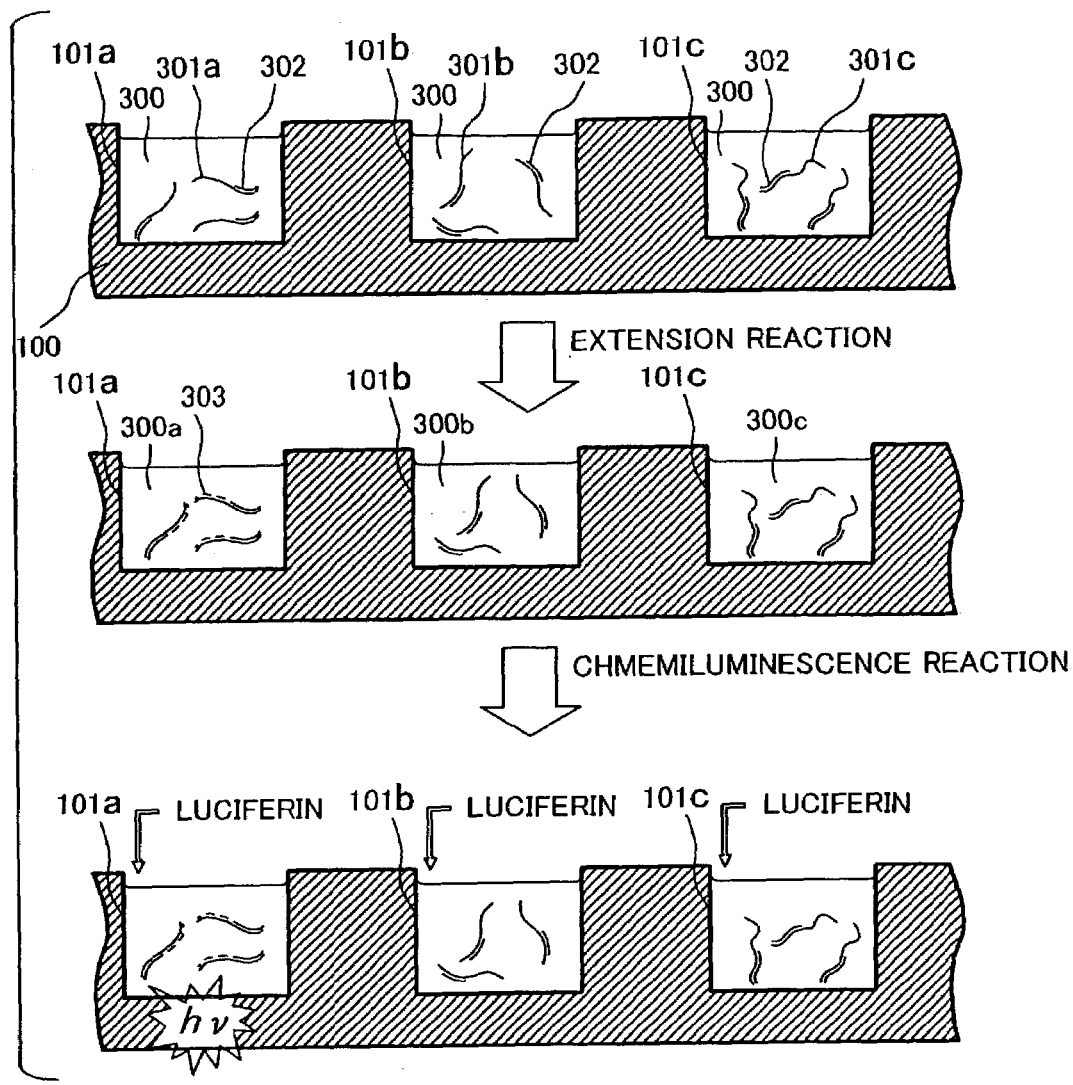
FIGS. 15A and 15B illustrate the flow of procedures when conducting the BAMPER technique described in Example 5 of the present invention.
Figure 15B:
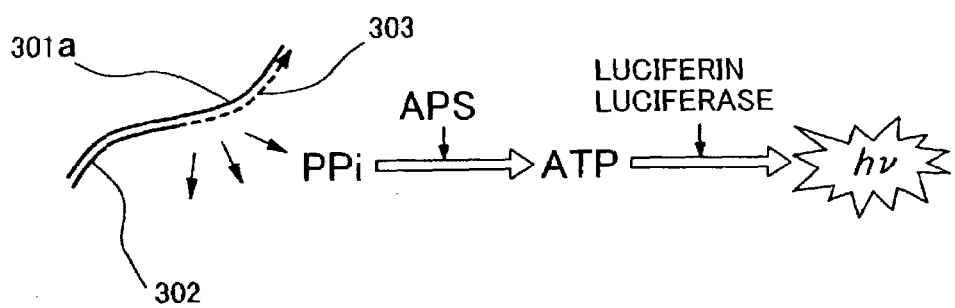

FIGS. 15A and 15B show an example of detection of SNPs by BAMPER using this sample. To the above-described reaction solution (4 μL) contained in reaction baths 101a–b were added base solution A (1 μL) and DNA sample solution (1 μL), and base extension reaction was then carried out. In this example, the primer 302 was the same for each of the reaction baths 101a–b, and 3 differing types of DNA samples 301a–c were instilled thereto. Approximately 10 sec after the start of reaction, base solution B (0.1 μL) was added thereto using a dispenser to start chemiluminescence reaction. A capillary tube was used in the dispenser. The diameter thereof was 25 μm and the capillary length was 21 mm. By varying the pressure and pressurization time, the amount of base solution added can be highly precisely controlled. In the case of an amount of 0.1 μL, the pressure was 0.2 Mpa and pressurization time was 1.1 sec. Extension reaction is controlled according to the presence of a match or mismatch at the primer terminus, and in the example illustrated in FIG. 15A, luminescence was observed in reaction bath 101a, thereby revealing that a sequence corresponding to the primer in this reaction bath was present on the target DNA.

Figure 16A:
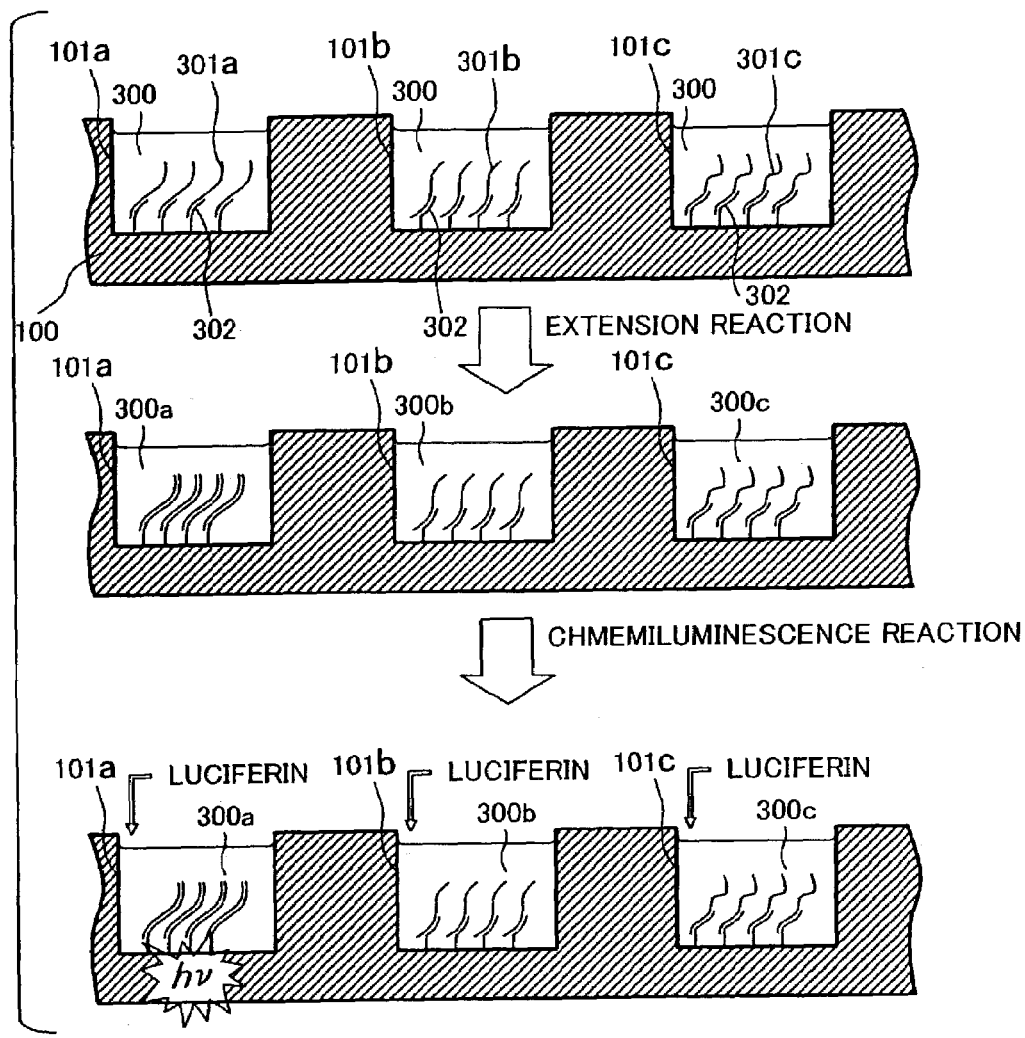
FIGS. 16A and 16B illustrate the flow of procedures when conducting the BAMPER technique with a probe immobilized in a reaction bath described in Example 5 of the present invention.
Figure 16B:
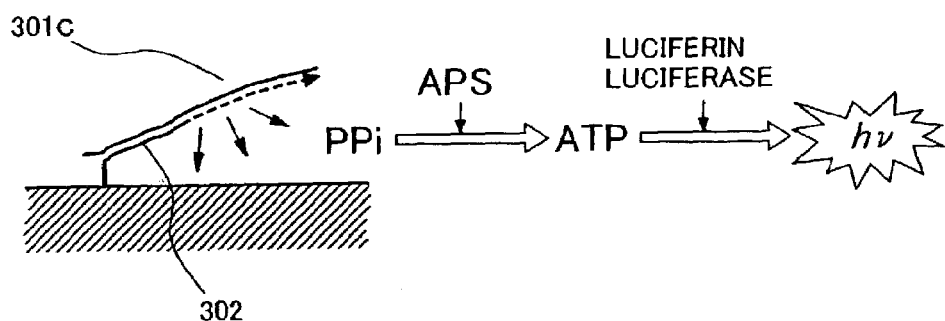

FIGS. 16A and 16B are an illustration of an example in which determination of SNPs was performed by immobilizing a primer in reaction baths 101a–c. A sample plate 100 is made of glass, and glycidoxypropyl groups are introduced onto the surface of subcells by an existing silane coupling reaction. The sample plate is immersed in 1 M NaOH and subjected to ultrasonic cleaning for 30 min. After washing under running water using ultrapure water, the sample plate is baked for 15 min at 110° C. Next, after soaking for 5 min in a stock solution of (3-glycidoxypropyl)trimethoxysilane, the sample plate is immersed for 30 min in a solution of 4% (3-glycidoxypropyl)trimethoxysilane dissolved in 50% ethanol solvent and stirred occasionally. The sample plate is then baked for 30 min at 110° C., to obtain a chip having glycidoxy groups introduced onto the surface of subcells using a silane-coupling reagent. 0.1 μL of various probes 302 (20 pmol/μL) is dissolved in a 0.5 M sodium bicarbonate buffer (pH 9.5), to obtain 1 pmol/μL. 0.5 μL of this DNA solution is instilled into subcells 101a–c on which surfaces a glycidoxy group is introduced. This is then heated at 50° C. for 30 min in the presence of saturated steam so as to prevent drying. It is then immersed in a 0.5 M sodium bicarbonate buffer (pH 9.5) of 0.1 M Lys to block residual glycidoxy groups. It is then washed with 20 mM Tris-HCl (pH 7.5). By the above operation, a probe 302 comprising several hundred bps is immobilized by reaction with amino group and glycidoxy group of the 5'-terminus. Base extension reaction and chemiluminescence reaction are conducted in the same manner as described in Example 5.

EXAMPLE 6

Figure 17:
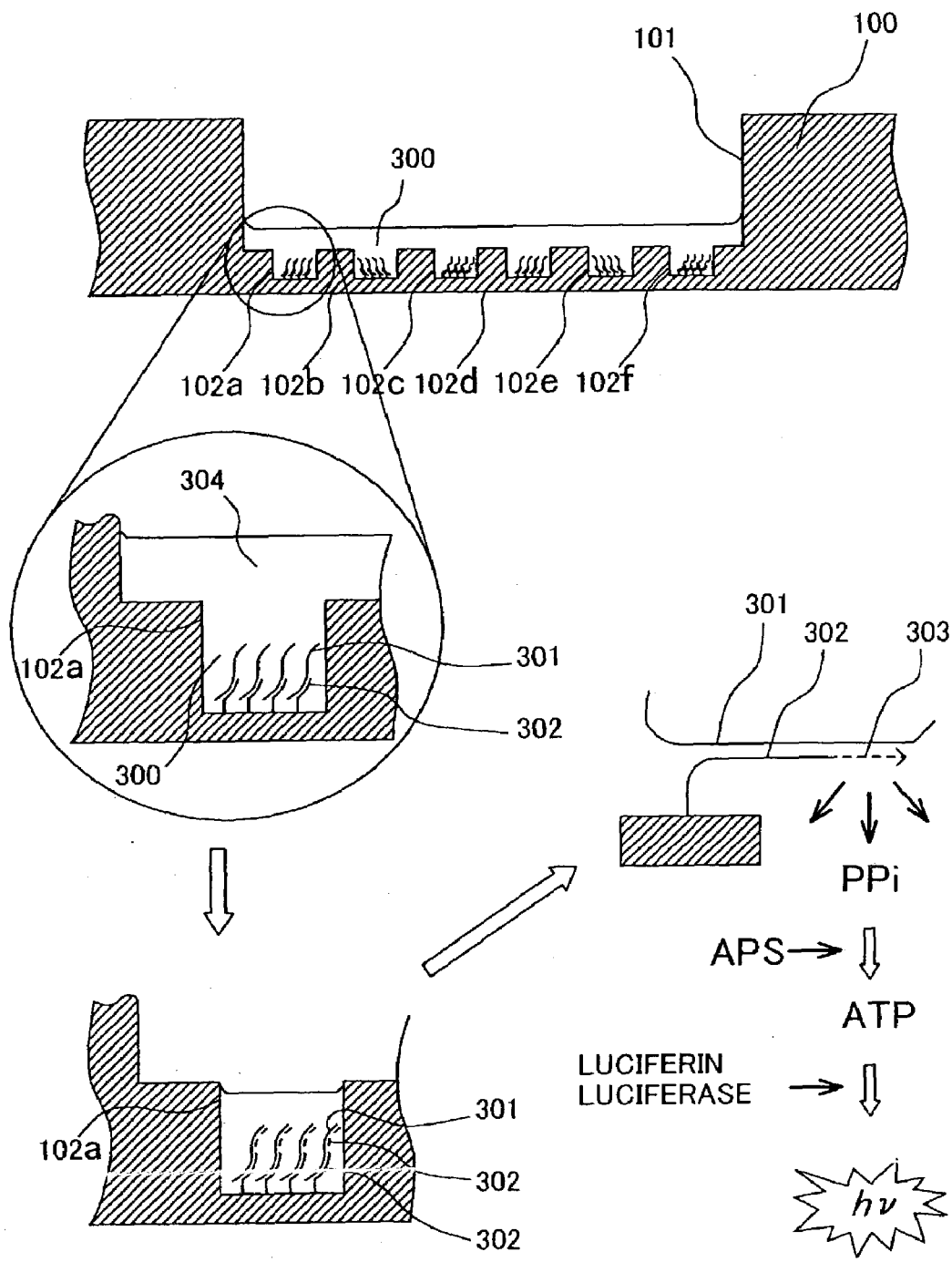
FIG. 17 shows the flow of procedures of the BAMPER technique when a plurality of subcells is provided inside one reaction bath and differing probes are immobilized therein, as described in Example 6 of the present invention.

FIG. 17 is an illustration showing an example of simultaneous assay of a variety of items by means of a reaction bath comprising subcells. Immobilization of probes to subcells 102a–f in the reaction bath is carried out using the same technique as in Example 5. By this operation, probe 302 comprising several hundred bps is immobilized in each subcell by reaction with amino group and glycidoxy group of the 5'-terminus.

As shown in FIG. 17, various probes are immobilized in each of subcells 102a–f by the above procedure. Here, extraction of DNA sample is carried out in the same manner as in Example 5, and then a reaction solution 300 containing a single-stranded DNA target 301obtained by treating double-stranded DNA 324, the PCR product, with NaOH, is distributed into each of reaction baths 101. At this stage, since the reaction solution can freely flow among the subcells, DNA capture can be performed efficiently by stirring the reaction solution. After DNA capture by hybridization, remove excess solution 304 and add reagent for complementary strand synthesis and reagent for chemiluminescence. At this point, ensure that the reaction solution is not allowed to mix between individual subcells. This is to prevent inorganic pyrophosphate generated by complementary strand synthesis in one subcell getting into a different subcell. Allow complementary strand synthesis 303 and chemiluminescence reaction and detect light.

Figure 18:
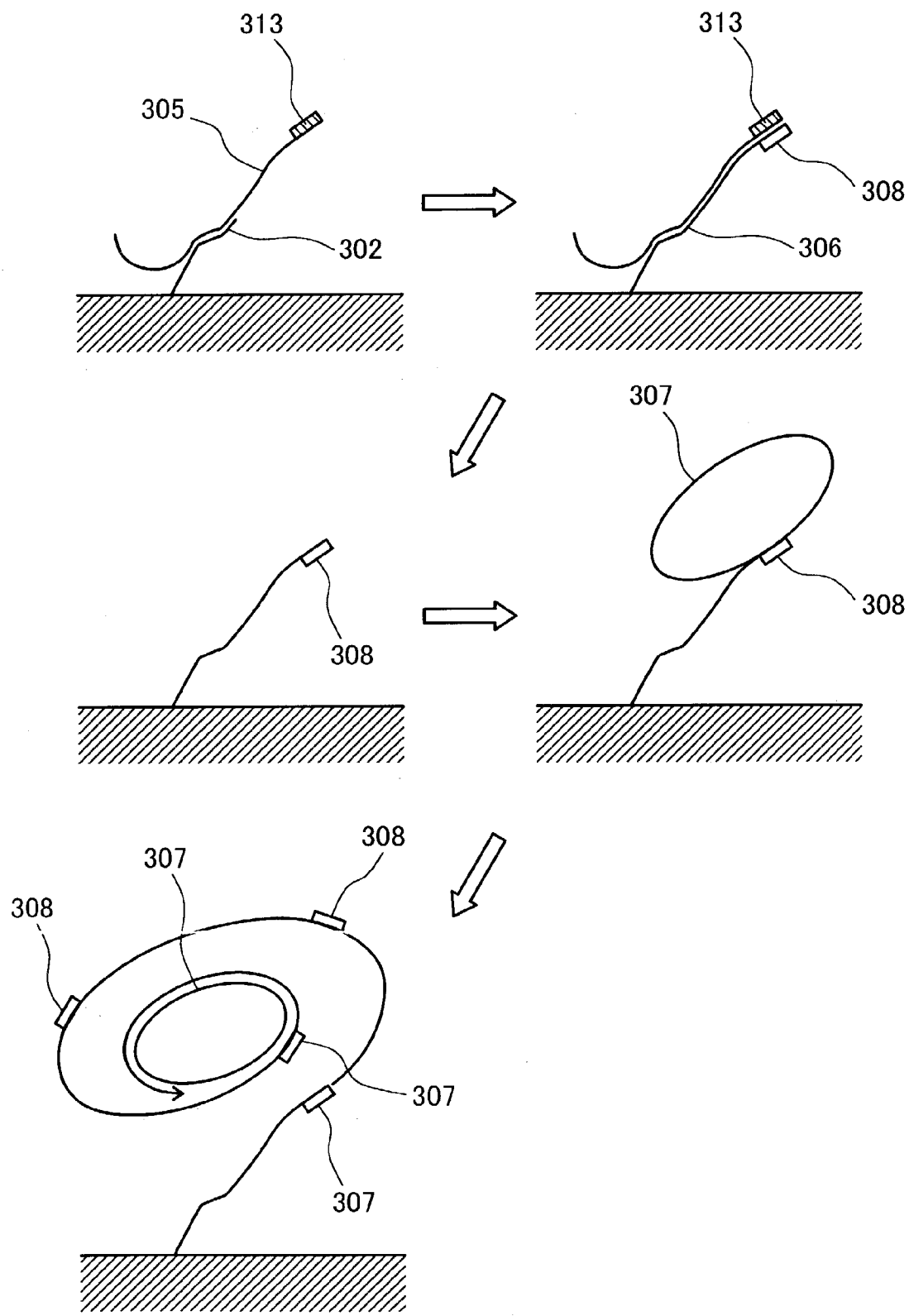
FIG. 18 illustrates the method of obtaining a large quantity of inorganic pyrophosphate by performing DNA complementary strand synthesis using circle DNA as a template described in Example 8 of the present invention.

In this case, a sample was prepared using PCR. However, rolling circle amplification or DNA amplification producing a loop (LAMP: Loop-mediated isothermal amplification of DNA; Nucleic Acids Research 2000, 28, e63) or the like may also be used. Specifically, as shown in FIG. 18, hybridize complementary strand 305 obtained from the genome by complementary strand and synthesis to immobilized probe 302, to obtain DNA strand 306 by complementary strand synthesis. Detection may also be performed of inorganic pyrophosphate obtained by hybridizing terminal sequence part 308 of the DNA strand using circular DNA 307 produced for assay as template and repeating complementary strand synthesis, or by producing template DNA having a loop sequence at its terminus and repeating complementary strand synthesis according to the LAMP method. In this case, since an extremely large amount of inorganic pyrophosphate is produced, high sensitivity can be obtained.

EXAMPLE 7

Figure 19:
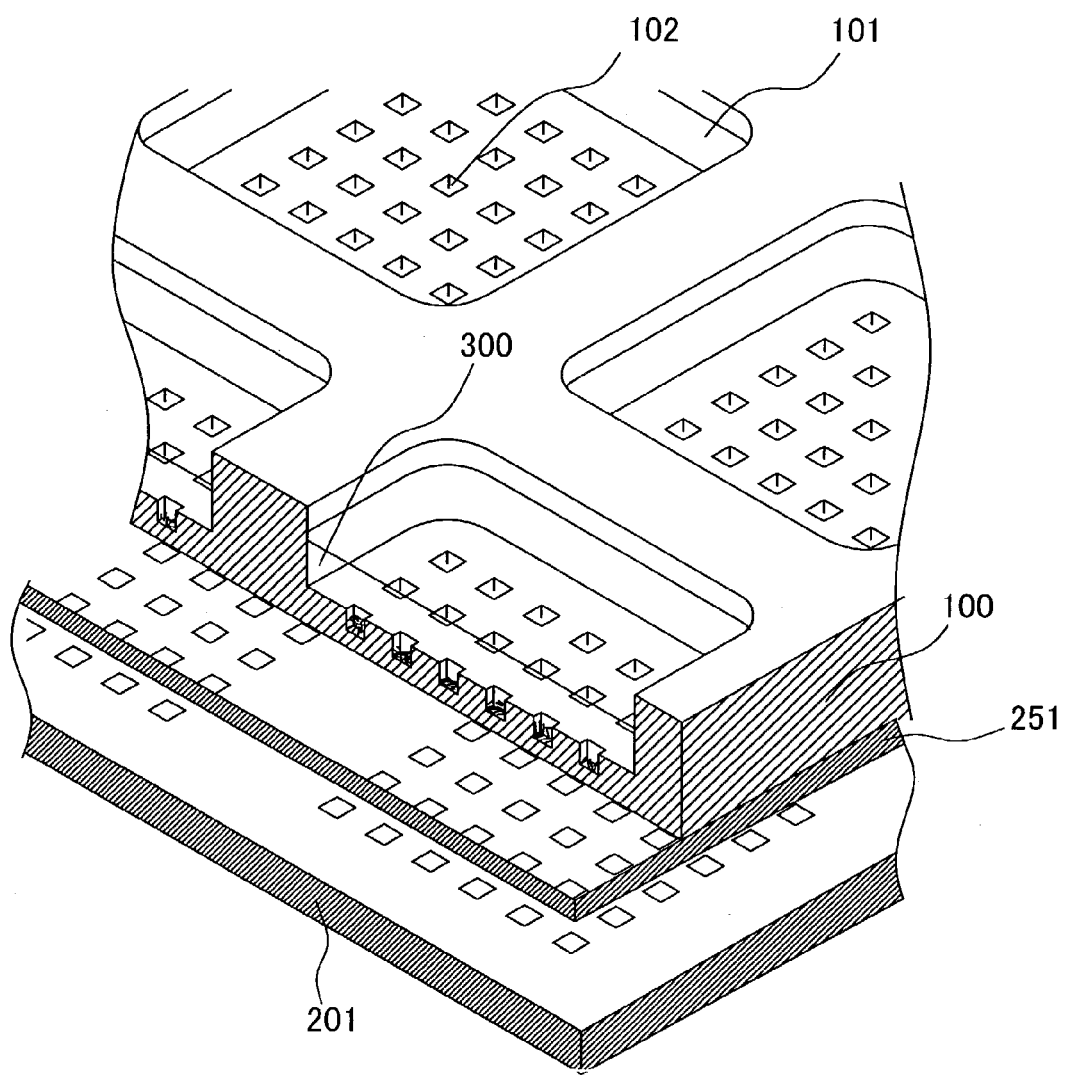
FIG. 19 is an illustration of the structure of the SNP assay apparatus utilizing reaction baths provided with subcells described in Example 9 of the present invention.
Figure 20:
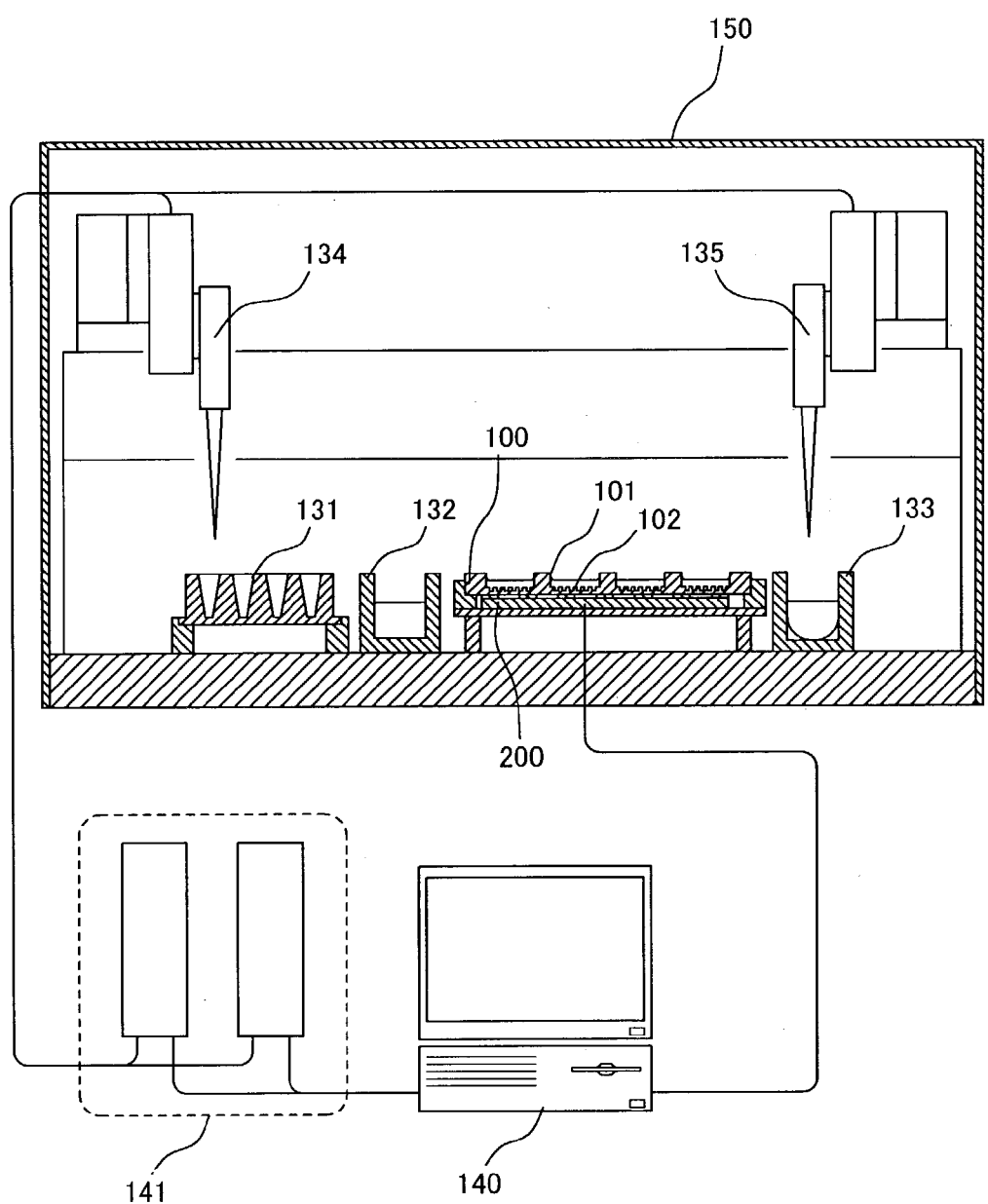
FIG. 20 is an illustration of an overview of the reaction baths comprising subcells and the optical sensor array according to the present invention.

The present example illustrates a means that performs complementary strand synthesis using a probe immobilized to a solid surface and detects chemiluminescence. FIG. 19 shows a configuration of the optical sensor array and sample plate having a large number of subcells inside reaction baths according to the present invention. FIG. 20 shows the conceptual structure of an entire system using the configuration shown in FIG. 19. The system comprises a sample plate 100, a chemiluminescence detection part 200, a reagent dispensing unit 134, and a data processing part 140. The sample plate comprises a plurality of reaction baths 101, and in the present example there are 96 reaction baths, and chemiluminescence can be observed from the bottom part or top part. Further, a plurality of subcells 102 is provided in the reaction baths. Inside reaction bath 101 having a basal area of about 1 cm$^2$, a total of 25–40 subcells 102 having a volume of about a sub-microliter arranged in rows at a 1-mm pitch.

A sample may be dispensed to the sample plate 100 before inserting it into the system. A sample solution containing a plurality of targets is dispensed into a reaction bath to fill the subcells with solution and conduct hybridization. The volume of a reaction solution is large enough for it to be retained inside the reaction bath in a condition in which it is overflowing from all the subcells. The solution is capable of moving inside the reaction bath, and by means of stirring hybridization is adequately performed. After removing excess solution, DNA polymerase, nucleic acid substrate (dNTP), luciferin, luciferase and the like are mixed together with a necessary reagent in a buffer and added thereto. Using a subcell separating plate, ensure that the reaction solution is separated into the individual subcells, so that inorganic pyrophosphate generated by complementary strand synthesis and luminescence reaction cannot move between the subcells. After putting a separating plate into the reaction bath 101 on a sample plate 100 so as to separate each subcell 102, set the sample plate to the system. Dispensing of a reaction reagent and separation of subcells by putting a cell separating plate into a reaction bath may also be performed within the system, however, when dealing a large number of titer plates, performing this operation outside of the measuring part of the system is preferable as a high throughput can be obtained. To retain the sample plate at a temperature that does not start complementary strand synthesis, a plate holder is to be temperature controlled such that the temperature thereof can be raised to start reaction after setting the sample plate into the system.

In the present example subcells 102 are of a shape that can hold solution, however, a flat plate shape in which probes are compartmentalized and immobilized on a flat plate may also be employed. In this case, complementary strand synthesis reaction can be carried out after the respective compartments in which probes are immobilized are separated using the above-described separating plate. Reagents for complementary strand synthesis and chemiluminescence can be compartmentalized by a separating plate after being dispensed into a reaction bath. Alternatively, reaction solution may be dispensed into each subcell by transfer tubes equipped to the separating plate.

As illustrated in FIG. 2, a primer immobilized in each subcell is a specific primer that can identify a mutation location, and after hybridizing to a target, complementary strand synthesis proceeds or does not proceed in accordance with the presence or absence of a nucleotide mutation. Thus, the generation of inorganic pyrophosphate is controlled. Specifically, inorganic pyrophosphate is converted to ATP, and in the reaction thereof with luciferin, luminescence is emitted, making it possible to identify a mutation by observing the luminescence. The starting time of a complementary strand synthesis reaction can be controlled by controlling the optimum temperature of enzyme. Since the peak intensity of chemiluminescence can be increased by starting a reaction after the primer hybridization has proceeded sufficiently, this system comprises a function that varies the temperature of the reaction part.

On the other hand, chemiluminescence may be obtained by using an immobilized primer only to capture a target, adding a primer that is sensitive to a mutation of a captured target to each subcell together with the matrix, and then hybridizing it to the target and performing complementary strand synthesis, or by using as a target a DNA strand obtained by complementary strand synthesis from an immobilized probe hybridized to the target and performing complementary strand synthesis again to generate inorganic pyrophosphate.

At least a subcell site in which a probe is immobilized is transparent, and chemiluminescence can be detected from the bottom part thereof. A separating plate having a shape covering a luminescence part is designed to reflect light such that a greater amount of light enters a photosensitive part. When performing detection of light from the top, a probe retainer is made such that it reflects light and the separating plate overlying the top is transparent.

EXAMPLE 8

The present example illustrates a case of retaining a probe in a subcell together with matrix. In this case, a probe is not immobilized and reaction is conducted entirely in liquid phase. A matrix containing probes corresponding to differing targets is previously supplied to each subcell by an ink-jet method or the like. A mixed solution of the target DNA, DNA polymerase, nucleic acid substrate (dNTP or analogs thereof), chemiluminescence reagent, buffer solution and the like is dispensed into the cell, and after separating the subcells by means of a separating plate, the temperature is raised to conduct reaction. Glycerol or agarose gel melted at a temperature of about 40–50° C. is used as a matrix. While a primer is retained in the matrix at room temperature or below, at the complementary strand synthesis temperature it is released in the reaction solution and used in synthesis of the complementary strand. This is a liquid phase reaction, and the reaction efficiency hereof is higher than that of reaction using an immobilized probe. Further, when using PCR using a primer specific to a target recognizing an SNP and a common primer, rolling circle DNA amplification, or the like, a large amount of inorganic pyrophosphate is generated, which enables enhancement or the detection sensitivity. This is made possible by the fact that the individual subcells are separated.

Figure 21:
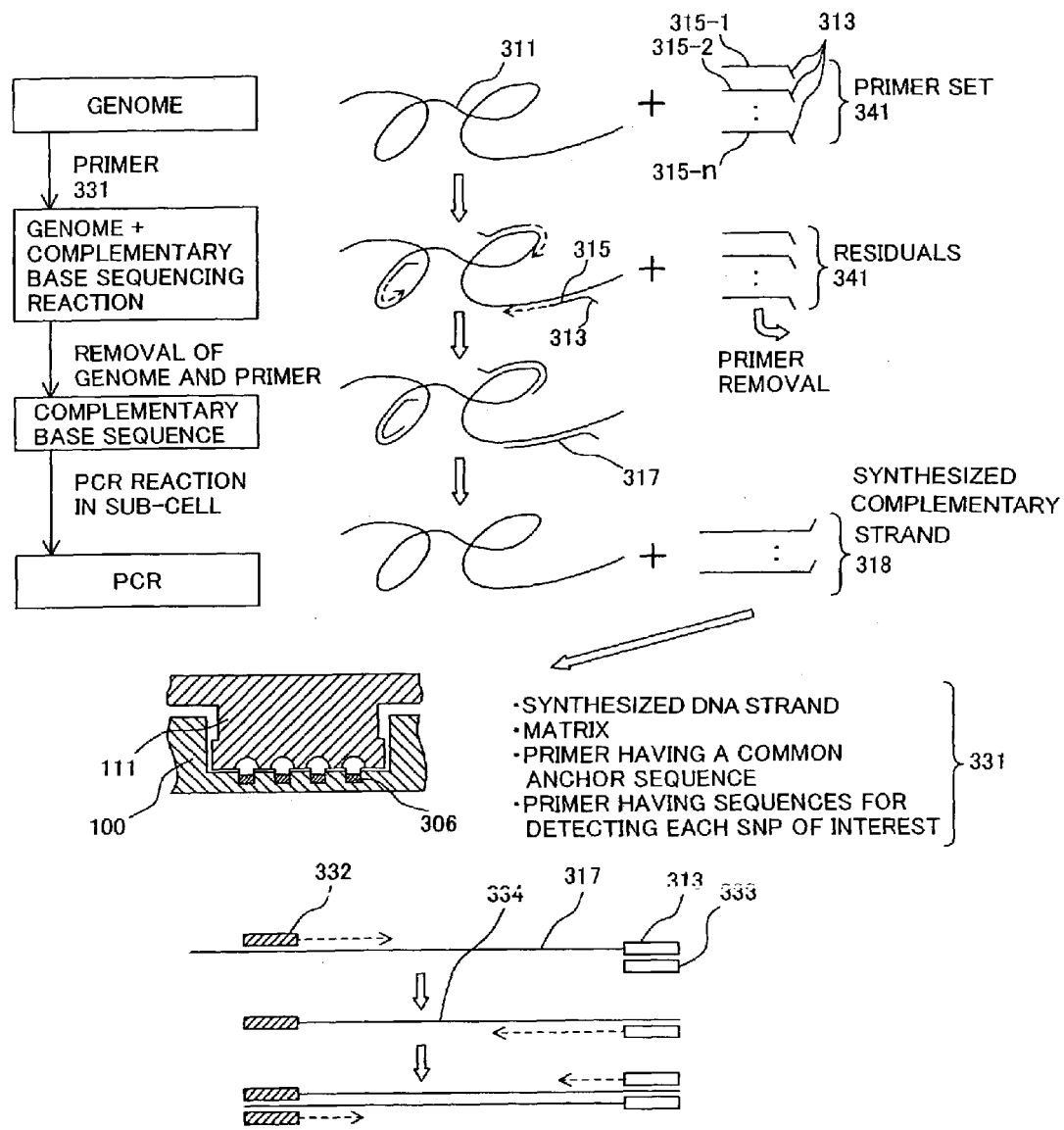
FIG. 21 shows the flow of procedures of an assay method that analyzes a variety of targets in one operation using the subcells according to the present invention.

FIG. 21 shows a schematic of sample preparation in detection of SNPs which combines this type of amplification of a target. Primers (probes) 341 specific to targets are hybridized to genome DNA 311, the assaying object, and complementary strand synthesis is conducted. At this point, the primers have a common anchor sequence (a sequence common to various primers) 313 at their 5'-terminus. After synthesis of the complementary strand, excess primers are removed. DNA strand 317 synthesized by complementary strand synthesis from the genome is extracted and inserted into a reaction bath together with other reagents 331. The common primer has an identical sequence to the anchor part, and after a complementary strand of the synthesized DNA strand is made, the primer is hybridized thereto to carry out complementary strand synthesis. A probe that is complementary to a respective target of interest is contained in each subcell, and only a specific DNA fragment is amplified. A primer capable of determining a mutation that can hybridize specifically to a target and synthesize a complementary strand is present, and a common primer can find a site at which hybridization is possible in DNA in a subcell only when complementary strand synthesis takes place. Inorganic pyrophosphate is generated every time complementary strand formation with an amount corresponding to the length of the complementary strand. Complementary strand synthesis is carried out in PCR amplification mode. The inorganic pyrophosphate is converted to ATP and this is used in a chemiluminescence reaction with luciferin. Light generated by the reaction is separated from light from adjacent subcells by separating plate 111and detected. The light passes through the transparent sample plate comprising subcells and reaction baths and is observed. In some cases herein it is not necessary to use a primer in which an artificial mismatch is inserted as a primer that is specific to a target. This is because in a process that repeats complementary strand synthesis reaction, a primer with matching terminal nucleotides hybridizes to a target at a higher frequency to increase the rate of reaction, and the PCR product is produced as the main product. Further, use of rolling circle DNA amplification or the like instead of PCR is effective. In particular, as dNTP pyrolytically decomposes at a high temperature to generate inorganic pyrophosphate, and imparts background light, the use of a DNA amplification method that acts at a temperature of 70° C. or below is effective.

EXAMPLE 9

Figure 22A:
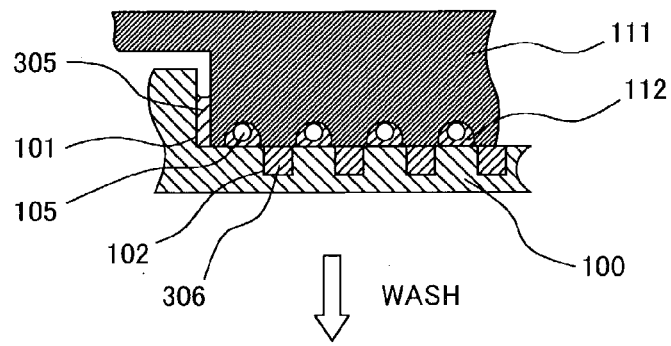
FIGS. 22A to 22C are an illustration of the constitution of the sample plate combining subcells and beads according to the present invention.
Figure 22B:
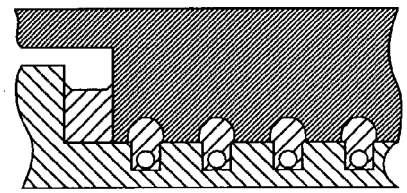
Figure 22C:
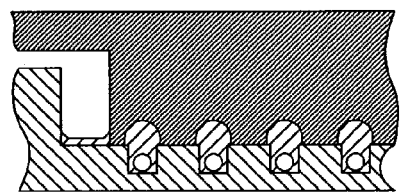

The present example describes a method using a bead to which a probe is immobilized. A bead is inserted into a subcell, and reaction is conducted in the same manner as in the previous example. Glass beads or plastic beads or the like can be used as the beads. The following description concerns the use of beads having a diameter of 100 μm, although glass beads of 10–100 μm in diameter can be used in the present example. A bead 105 is used after a probe is immobilized thereto. The same method as that in Example 6 is employed to immobilize a probe to the surface of a glass bead. As illustrated in FIG. 22, beads 105 with a probe immobilized thereto are fixed in a retainer 111 having hollows 112 by a soluble material, such as glycerol, to construct a bead probe array. The probe array includes DNA probes corresponding to the DNA sites of interest. This is inserted into the respective reaction baths. The array of beads with probes and the position of the reaction baths are brought into correspondence. Subcells 102 are provided in a reaction bath 101, but initially hollows 112 of the retainer and subcells 102 are allowed to be misaligned with respect to each other, so that beads 105 do not enter subcells 102 (FIG. 22A). Introduce a solution 305 containing targets into reaction bath 101 and adequately conduct hybridization. Thereafter, move the retainer 111 (FIG. 22B) to insert beads 105 into the subcells, and insert reagents necessary for complementary strand synthesis and chemiluminescence reagents (FIG. 22C) and conduct reaction. Since chemiluminescence reaction takes place only within the subcells, it is possible to recognize and detect a signal originating from complementary strand synthesis performed employing a target captured on an individual bead as a template. The kind of probe can be known from the site having luminescence, and the amount of a target hybridized to the probe can be known from the luminescence intensity. Only one bead may be inserted into each subcell, or a plurality of beads may be inserted therein.

EXAMPLE 10

Figure 23:
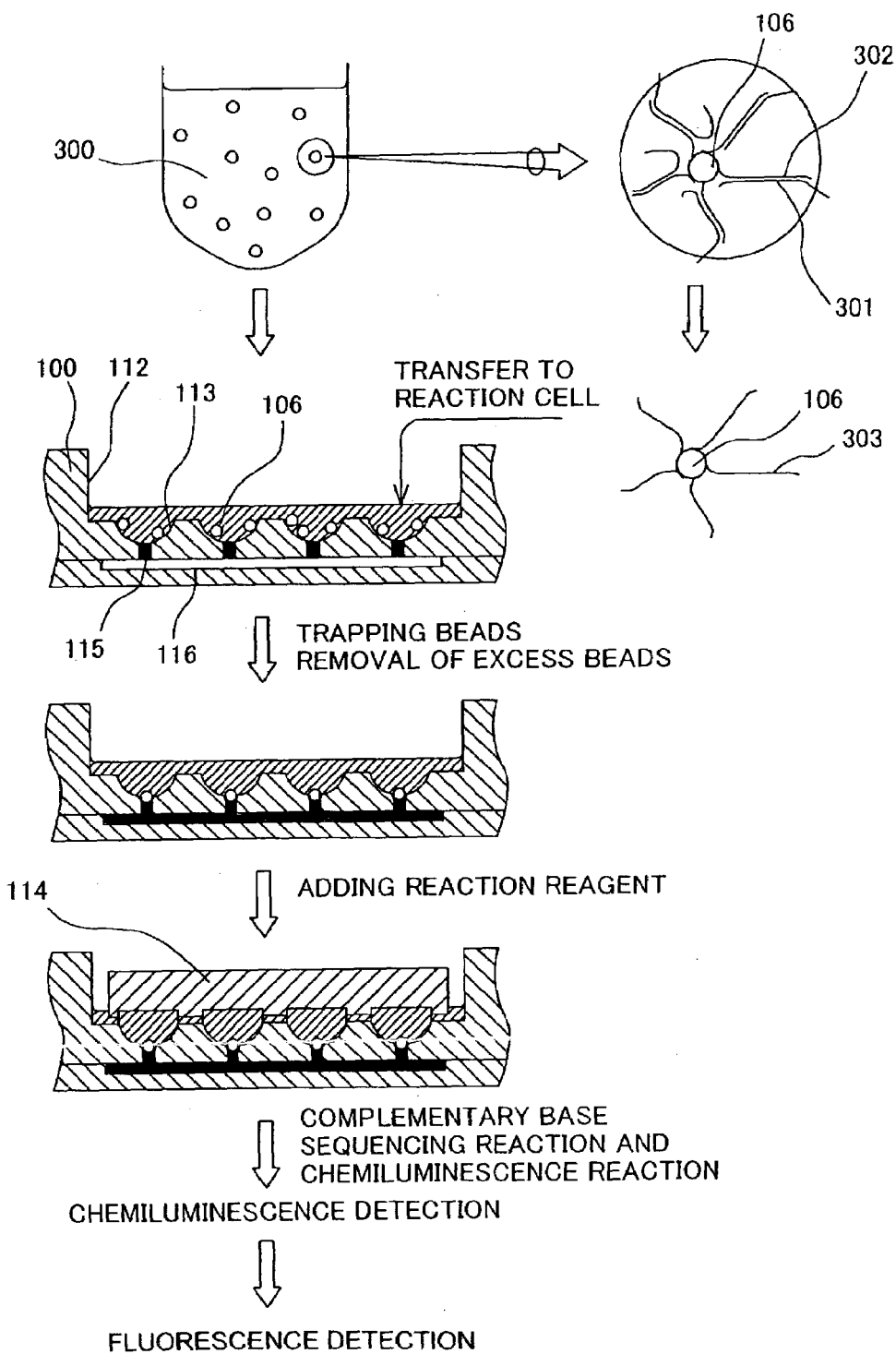
FIG. 23 shows the flow of procedures of the assay method using color-coded beads according to the present invention.

The present example describes a method using color-coded beads. DNA probes are brought into correspondence with beads having respectively different color codes, and immobilized to the surface thereof. In the detection of inorganic pyrophosphate generated at the time of complementary strand synthesis, it is necessary to hybridize a target to a probe and perform complementary strand synthesis to a high degree of efficiency. In comparison to a probe immobilized to the surface of a planate solid object, a probe immobilized to a bead capable of floating in a reaction solution provides significantly enhanced hybridization efficiency. The present method conducts hybridization in solution, but thereafter traps the bead in a subcell in the reaction bath to detect chemiluminescence. FIG. 23 illustrates this example. The bottom part of a subcell 113 comprises a hole 115 for suction and discharge of solution, and each hole is connected to a connecting piping 116. Depressurizing connecting piping 116 allows color-coded beads 106 to be captured in each subcell 113. Identification of the kind of probe immobilized on color bead 106 is performed by reading the color of the bead. Specifically, the color code is read after detection of fluorescence due to irradiation of light, and the amount of the target is determined from the chemiluminescence. Measurement using color-coded beads and fluorescently labeled targets has been reported heretofore, however, while fluorescence emitted from color-coded beads is extremely strong, light emitted from fluorescence labeled to a target is not strong. Consequently, highly accurate measurement has not been possible. In the present method, determination of fluorescence is performed after completing determination of chemiluminescence or in advance thereof. Thus, by ensuring that determination of chemiluminescence is not carried out during irradiation of light, high sensitivity detection and coding by optical measurement of beads are realized.

As a laser for reading codes, a red laser having a luminescence wavelength of 650 nm is used, and a green or blue laser or the like may also be used. After extending the laser one time, it is irradiated as multiple spots on beads captured in cells in a reaction bath by means of a microlens array. The fluorescence is condensed by the lens, and after passing through a filter is received by an area sensor or line sensor such as a cooled CCD or the like. The fluorescence is observed by allowing it to alternately pass through 2 or 3 kinds of filters having differing transparency wavelength bands that correspond to the wavelengths of the color coded dyes, or by adjusting the lens such that the fluorescence reaches a plurality of photodetective pixels, and using filters of differing transparency wavelengths placed in front of the respective light-receptive pixels to read the color codes by separating the wavelengths and receiving the light. Remove the filters when measuring chemiluminescence. Perform complementary strand synthesis reaction and chemiluminescence reaction by separating the respective subcells using a separating plate. In this example, nucleic acid substrate and DNA polymerase required for complementary strand synthesis and chemiluminescence reagents and the like are fed into a reaction bath from a capillary tube 115 in the bottom part of the hole in which a bead is trapped. However, each subcell may also be separated by a separating plate after reagents are dispensed uniformly into the entire reaction bath. Detection of light of a subsequent reaction is carried out in the same manner as in the previous example.

EXAMPLE 11

Figure 24:
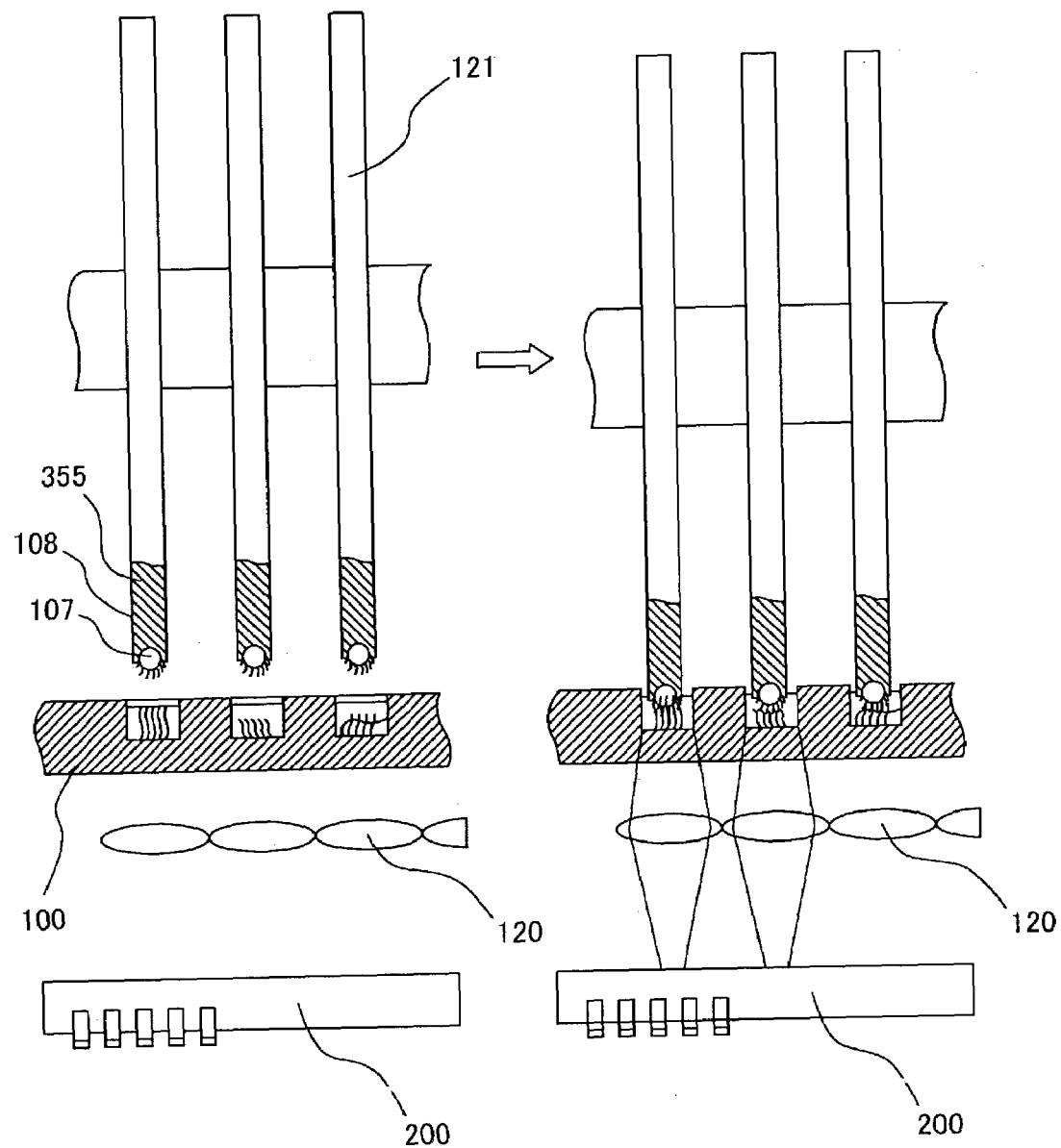
FIG. 24 shows a cross-section of the constitution of the reaction baths using fiber described in Example 11 of the present invention.

As described above, the third feature of the present invention involves immobilizing a DNA probe on a material such as beads or fiber that can be divided into individual parts, carrying out highly efficient hybridization reaction in one reaction bath in one batch, and subsequently carrying out complementary strand synthesis and detection of chemiluminescence in a separated state. In addition to beads, various materials can be used as probe carriers, including a fiber tip, wire and the like. An example of this is shown in FIG. 24. The tip of an optical fiber 121 is used as a probe immobilization part. A similar result can be obtained by attaching a probe to a wire-shaped material and enclosing it in a capillary instead of the present optical fiber. In the example using a fiber, a probe is directly attached to the fiber tip and the fiber tip is etched to retain a probe therein together with a bead or matrix. In order to carry out complementary strand synthesis reactions in a condition in which the reactions are separate from each, as shown in FIG.

24, a probe retaining part fabricated in the fiber tip is such that it can be divided into subcells. That is, a shallow reaction bath having one hole that is almost the same as a bead 107 is used. Only one bead 107 is trapped in the hole, and only one kind of probe can enter the reaction bath of each fiber tip. The subsequent reaction is as previously described. On the other hand, by providing the same type of reaction bath in a wire or thin rod and immobilizing a probe therein and inserting it all into a capillary tube, a capillary shaped reaction bath 108 having many reaction baths therein can be made. FIG. 24 shows a cross-section of the capillary shaped reaction bath 108. The reaction baths are connected by a narrow channel, and disposed such that a reaction solution 355 passes through the reaction baths. In the reaction baths, a probe is retained by being immobilized to a bead or to the surface of the reaction bath. With respect to the DNA probe, when a target is flowed through the cell for hybridization it is necessary for the probe to be immobilized, but in subsequent reactions, because the cells are separated, it is not necessary for the probe to remain in an immobilized state. For example, bonding which can be separated by heating, such as in antigen-antibody bonding, may be used. After hybridizing, reagents for complementary strand synthesis and chemiluminescence are dispensed therein. Dispensing of reagents is done at a temperature sufficiently low enough for it to be difficult for complementary strand synthesis reaction to occur (generally, a substantial reaction can be suppressed by cooling on ice). Dispense the reagents and prevent reaction from proceeding during the dispensing. After dispensing, raise the temperature to the optimum temperature for reaction, to carry out complementary strand synthesis reaction and chemiluminescence reaction.

EXAMPLE 12

Figure 25A:
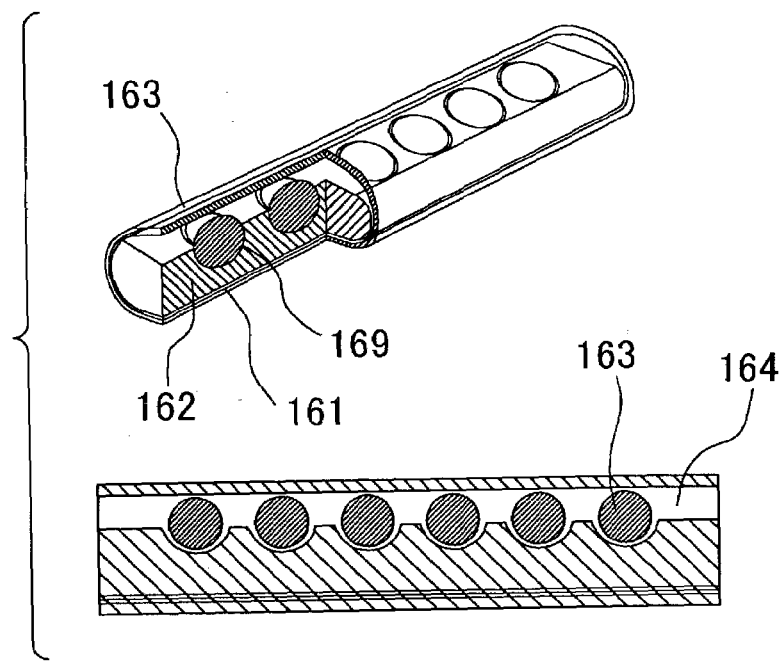
FIGS. 25A and 25B are illustrations of a reaction bath of a type into which a grooved rod holding beads in capillaries is inserted, as described in Example 12 of the present invention.
Figure 25B:
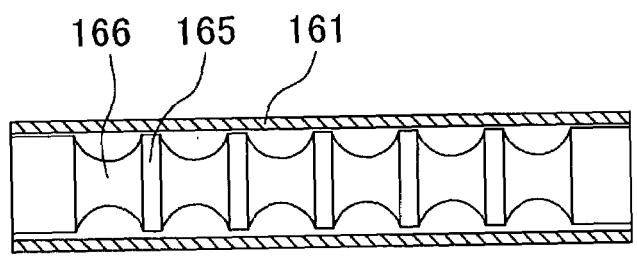
Figure 25C:
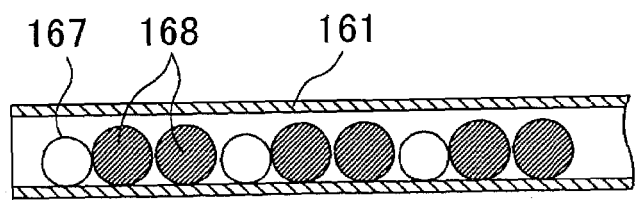
FIG. 25C is an illustration of a reaction bath of the type in which separating beads and probe beads are arranged alternately in a capillary, as described in Example 17 of the present invention.

In the example illustrated in FIGS. 25A to 25C, hollows 169 are formed in an array form in a rod-shaped holder 162, and the holder is inserted in a capillary 161. Beads 163 are contained in these holes. The specific method of construction involves forming hollows 169 or holes 166 in a rod-shaped holder, retaining the beads 163 in the hollows 169 or holes 166, and inserting the holder into capillary 161. Alternatively, spacer beads 168 may be introduced between beads with probes 167 inside a capillary, and the kinds of probes on the beads then identified.

EXAMPLE 13

Figure 26:
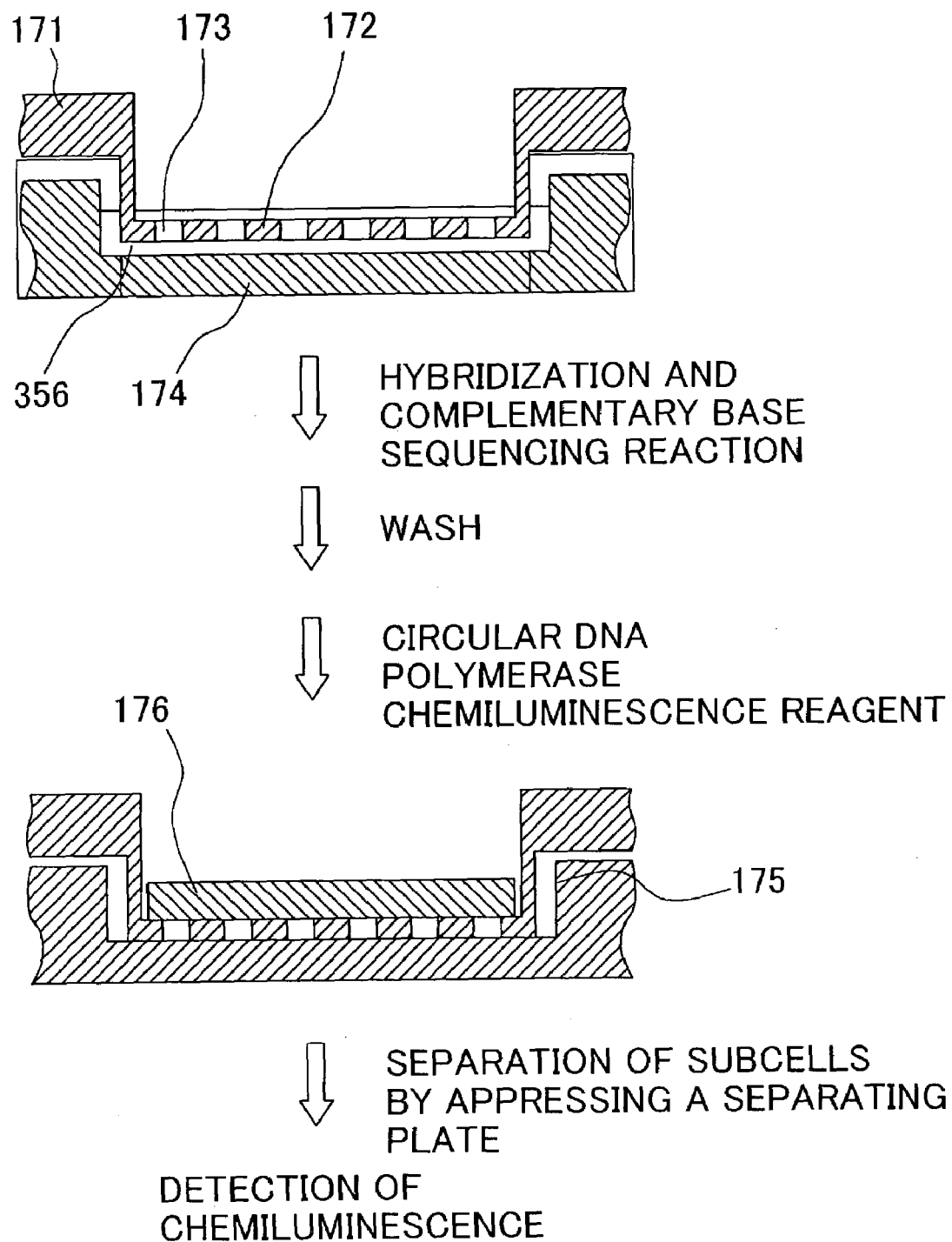
FIG. 26 is an illustration of an example using a microchannel as a probe holder described in Example 13 of the present invention.

FIG. 26 is an illustration of an example using a microchannel as a probe holder. Probes are immobilized to a wall part or the like of holes of several microns—several hundred microns (perforated holes) 173 provided in a plate, and these holes are used as reaction subcells. To increase the amount of DNA immobilized in the hole, a suitable method is to fill the hole with a porous element or to retain a bead therein. The present example describes the case of a plate having a simple hole 173. Provide a hole at the base of a sample plate and immobilize a probe to a wall of the hole. Here, a plurality of minute holes may be provided or only one hole may be provided. In one reaction bath, 30–40 holes 173 (these are reaction subcells, wherein the subcells are spatially separate from each other) are provided. As a different DNA probe is immobilized in each subcell, the amount of DNA that can be assayed is equivalent to the number of subcells. To this reaction bath add solution containing targets and carry out hybridization and complementary strand extension reaction. To efficiently conduct hybridization in this situation, allow a solution 356 to flow up and down in a tray 174 disposed thereunder. After reaction is completed, remove the solution containing the targets, or move a sample plate 171 to a different, adhering-type tray. Add circular DNA and DNA polymerase, chemiluminescence reagents and the like thereto, and carry out generation of inorganic pyrophosphate (complementary strand synthesis using circular DNA as template) and chemiluminescence reaction in each subcell. As the subcells are separated by an adhering-type tray and a separating plate 172, luminescence produced by a reaction in each subcell is separated and can be observed.

For detection of chemiluminescence, in addition to the use of a line sensor or area sensor described previously herein, detection can also be performed by moving a light-sensitive detector using a photomultiplier tube or the like and a titer plate relative to each other to detect luminescence.

As described above, the present invention enables simple detection of a target using a plurality of probes. In the genetic testing system of the present method a plurality of target DNA regions are simultaneously amplified in one batch and inserted into a reaction bath, where each region of interest can be independently assayed using a variety of probes. There is not used in detection, there is an advantage that a large number of assay sites can be simply assayed using a low-cost system. In contrast to a method employing only hybridization of a DNA chip or the like, in the present system a process of complementary strand synthesis is undergone following hybridization, thus enabling much higher detection accuracy. Consequently, the present invention can also be used in assay of single nucleotide polymorphisms or the like in a nucleotide sequence. There is also an advantage that operations are simple, as after extraction of DNA from a blood sample, reactions are performed in the same reaction bath.

What is claimed is:

1. An apparatus for luminometric assay, comprising:
  a sample plate in which a plurality of reaction baths containing a biological sample are arranged one-dimensionally or two-dimensionally;
  an optical sensor array substrate comprising an optical sensor array in which a plurality of pixels each forming an optical sensor are arranged one-dimensionally or two-dimensionally, and a first pixel selecting circuit and a second pixel selecting circuit for selecting pixels that read out signals;
  a member fixing the sample plate and the optical sensor array substrate such that the reaction baths and the pixels are in a one-to-one correspondence in a vertical direction; and
  a single differential amplifier unit which differentially amplifies an output from a first pixel selected by the first pixel selecting circuit and an output from a second pixel selected by the second pixel selecting circuit,
  wherein the first pixel and the second pixel are used for detecting signals corresponding to a target sample and a control sample so as to generate the outputs, respectively, and
  lights generated by reactions between the target and control samples with a reagent in reaction baths corresponding to the first and second pixels are received by the optical sensors of the pixels, and the signals from the pixels are read out.

2. The apparatus for luminometric assay according to claim 1, wherein the first pixel selecting circuit and the second pixel selecting circuit select a plurality of the pixels independently from each other.

3. The apparatus for luminometric assay according to claim 1, wherein a distance between a plane of incidence of light of the optical sensor array substrate and a surface of a bottom side of the reaction baths of the sample plate is 3 mm or less, or, wherein a transparent member with an optical waveguide function or a lens function is disposed between the plane of incidence of light of the optical sensor array substrate and the surface of the bottom side of the reaction baths of the sample plate such that the plane of incidence of light of the optical sensor array substrate and the surface of the bottom side of the reaction baths of the sample plate are optically coupled.

4. An apparatus for luminometric assay, comprising:
  a sample plate in which a plurality of reaction baths containing a biological sample are arranged one-dimensionally or two-dimensionally;
  an optical sensor array substrate comprising a photodiode array in which a plurality of pixels each forming a photodiode are arranged one-dimensionally or two-dimensionally, and a first pixel selecting circuit for selecting a first one of the pixels that reads out a signal corresponding to a target sample, and a second pixel selecting circuit for selecting a second one of the pixels that reads out a signal corresponding to a control sample;

a member fixing the sample plate and the optical sensor array substrate such that the reaction baths and the pixels are in a one-to-one correspondence in a vertical direction; and a single differential amplifier unit which differentially amplifies an output from the first pixel selected by the first pixel selecting circuit and an output from the second pixel selected by the second pixel selecting circuit, wherein a light generated by a reaction in a first one of the reaction baths corresponding to the first pixel is received by the photodiode of the first pixel, and a light generated by a reaction in a second one of the reaction baths corresponding to the second pixel is received by the photodiode of the second pixel, and the signals from the first and second pixels are read out at the same time.

5. The apparatus for luminometric assay according to claim 4, wherein each of the pixel selecting circuits is a decoder randomly selecting the pixel time sequentially or a shift register selecting the pixel time sequentially in a prescribed order.

6. The apparatus for luminometric assay according to claim 4, wherein the signal read out from the second pixel is in a dark state.

7. The apparatus for luminometric assay according to claim 4, wherein in accordance with an intensity of the light generated in the second reaction bath containing the control sample to be assayed or a value of dark current of the photodiode of the second pixel, a signal storage time is changed in the first and second pixels to perform a zero point correction of an output of the single differential amplifier unit.

8. The apparatus for luminometric assay according to claim 4, wherein each of the pixels comprises first, second and third MOS transistors, the signal from the photodiode of said each pixel is input to a gate of the first MOS transistor, whereby a source follower circuit is comprised, a voltage of the photodiode is followed by a source, a drain of the second and third MOS transistors connected to a source of the first MOS transistor, an output terminal of the first pixel selecting circuit is connected to a gate of the second MOS transistor, an output terminal of the second pixel selecting circuit is connected to a gate of the third MOS transistor, a source of the second MOS transistor is connected to a first output signal line, a source of the third MOS transistor is connected to a second output signal line, a load resistance or a constant-current source is connected to the first and second output signal lines, and a plurality of pixels are independently selected by the first and second pixel selecting circuits, and wherein control is performed such that a signal is output to the first and second output signal lines.

9. The apparatus for luminometric assay according to claim 4, comprising a transparent conduction film between the surface of the bottom side of the reaction baths of the sample plate and the surface of a photo-receptive side of the optical sensor array substrate.

10. An apparatus for luminometric assay, comprising:
a sample plate in which a plurality of reaction baths containing a biological sample are arranged one-dimensionally or two-dimensionally, wherein the respective reaction baths comprise a plurality of subcells in the bottom part thereof;

an optical sensor array substrate comprising a photodiode array in which a plurality of pixels comprising a plurality of photodiodes are arranged one-dimensionally or two-dimensionally;

a member fixing the sample plate and the optical sensor array substrate such that the reaction baths and the pixels are in a one-to-one correspondence in a vertical direction;

a first pixel selecting circuit for selecting a first one of the pixels that reads out a signal corresponding to a target sample, and a second pixel selecting circuit for selecting a second one of the pixels that reads out a signal corresponding to a control sample; and a single differential amplifier unit which differentially amplifies an output from a first pixel selected by the first pixel selecting circuit and an output from a second pixel selected by the second pixel selecting circuit, wherein at least one DNA probe and/or a reagent is contained in each of the plurality of subcells of the respective reaction baths, and lights generated by reactions of the target and control samples with the DNA probe and/or the reagent in the respective subcells of the respective reaction baths are detected.

11. The apparatus for luminometric assay according to claim 10, wherein a plurality of the photodiodes are selected independently from each other by the first pixel selecting circuit and the second pixel selecting circuit.

12. The apparatus for luminometric assay according to in claim 10, wherein the biological sample is contained in the reaction baths, and in each of the plurality of subcells of the reaction baths containing the DNA probes are immobilized, the DNA probe in one respective subcell is a respectively different kind from the kinds in other subcells, and wherein inorganic pyrophosphate generated in the plurality of subcells by complementary strand synthesis in which each of the DNA probes is bound to the biological sample by complementary strand binding does not mix among the plurality of subcells.

13. The apparatus for luminometric assay according to claim 10, further comprising means supplied to the respective subcells of the respective reaction baths, as substrates for use in complementary strand synthesis including a plurality of kinds of nucleotides or nucleic acid analogs in a mixed state.

14. The apparatus for luminometric assay according to claim 10, wherein a color-coded bead to which is immobilized the DNA probe or the biological sample, which is a target, is immobilized in each of the plurality of subcells of the reaction baths, and on the DNA probe immobilized to the bead the target is captured by complementary binding, or a primer is hybridized to the target immobilized to the bead, and wherein inorganic pyrophosphate generated by complementary strand synthesis carrying out extension of the DNA probe or the primer is converted to ATP, and chemiluminescence generated by a reaction of the ATP and a luminescent substance is respectively detected in each of the plurality of subcells of the reaction baths, and the color code of the bead is read.

* * * * *

SEQUENCE LISTING

<160> NUMBER OF SEQ ID NOS: 4

<210> SEQ ID NO 1
<211> LENGTH: 95
<212> TYPE: DNA
<213> ORGANISM: Artificial Sequence
<220> FEATURE:
<223> OTHER INFORMATION: Description of Artificial Sequence:
    Synthetic DNA -continued

```
<400> SEQUENCE: 1
ctttcttgcg gagattctct tcctctgtgc gccggtctct cccaggacag gcacaaacac      60
gcacctcaaa gctgttccgt cccagtagat tacca                                 95

<210> SEQ ID NO 2
<211> LENGTH: 95
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 2
ctttcttgcg gagattctct tcctctgtgc gccggtctct cccaggacag gcactaacac      60
gcacctcaaa gctgttccgt cccagtagat tacca                                 95

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 3
aacagctttg aggtgcgtga tt                                               22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 4
aacagctttg aggtgcgtga ta                                               22
```